United States Patent [19]

Iwasaki et al.

[11] Patent Number: 5,672,779
[45] Date of Patent: Sep. 30, 1997

[54] ESTER COMPOUND, ACTIVE AGENT FOR CONTROLLING NOXIOUS INSECT PESTS CONTAINING THE SAME AS ACTIVE INGREDIENT, INTERMEDIATE FOR PRODUCTION OF THE ESTER COMPOUND AND PROCESS FOR PRODUCING THE INTERMEDIATE

[75] Inventors: Tomonori Iwasaki; Masaya Suzuki; Takashi Furukawa, all of Takarazuka; Kazunori Tsushima, Sanda; Takao Ishiwatari, Minoo; Toru Tsuchiya, Takarazuka, all of Japan

[73] Assignee: Sumitomo Chemical Company, Limited, Osaka, Japan

[21] Appl. No.: 641,431

[22] Filed: May 1, 1996

Related U.S. Application Data

[62] Division of Ser. No. 294,934, Aug. 23, 1994, Pat. No. 5,550,258.

[30] Foreign Application Priority Data

Aug. 24, 1993 [JP] Japan .................................. 5-209742
Jun. 22, 1994 [JP] Japan .................................. 6-140004

[51] Int. Cl.$^6$ .................................................. C07C 13/12
[52] U.S. Cl. ...................... 568/838; 568/594; 568/667; 549/421; 549/475
[58] Field of Search .............................. 568/667, 594, 568/838; 549/421, 475

[56] References Cited

U.S. PATENT DOCUMENTS 4,304,733 12/1981 Martel et al. .
4,356,187 10/1982 Martel et al. .

FOREIGN PATENT DOCUMENTS 0018893 11/1980 European Pat. Off. .
0585063 3/1994 European Pat. Off. .
55-147233 4/1980 Japan .
56-156238 7/1980 Japan .

OTHER PUBLICATIONS

Patent Abstracts of Japan, vol. 6, No. 40 (C–94) May 1980 re JP–A 56–156238 (pub. Dec. 1981).

K. Takai, et al., "Wittig–type Reaction of Dimetallated Carbodianion Species as Produced by Zinc Reduction of gem–Polyhalogen Compounds in the Presence of Lewis Acids", Bull. Chem. Soc. Jpn., Vo. 53, 1980, pp. 1698–1702.

L. Lombardo, "Methylenation of Carbonyl Compounds With Zn–CH$_2$Br$_2$TiCl$_4$", Tetrahedron Letters, vol. 23, 1982, pp. 4293–4296.

Y. Ogawa, et al., "The Intramolecular Thermal ENE Reaction Route to (+)-9(0)-Methano-$\Delta^{6(9\alpha)}$-PGI$_1$", Tetrahedron Letters, vol. 25, No. 10, 1984, pp. 1067–1070.

R. Jacobs, et al., "Defense Mechanisms of Arthropoeds. 84. Synthesis of (–)-α-Necrodol and (–)-B-Necrodol: Novel Cyclopentanoid Terpenes from a Carrion Beetle", J. Org. Chem., vol. 55, 1990, pp. 4051–4063.

L. Lombardo, et al., "A New Strategy for C$_{20}$ Gibberellin Synthesis: Total Synthesis of (±)-Gibberellin A$_{38}$ Methyl Ester", J. Org. Chem., vol. 48, No. 13, 1983, pp. 2298–2300.

J. Hibino, et al., "Carbonyl Methylenation of Easily Enolizable Ketones", Tetrahedron Letters, vol. 26, No. 45, 1985, pp. 5579–5580.

L. Lombardo, et al., "Methylenation of Carbonyl Compounds: (+)-3-Methylene-cis-p-Menthane (Cyclohexane, 4-methyl-2-methylene-1-(1-Methylethyl)-, R,R-)", Org. Synth., vol. 65, 1987, pp. 81–89.

Okazoe et al, 'Chemoselective Methylenation with a Methylendedianion Synthon', Tetrahedron Letters, vol. 26, No. 45, pp. 5581–5584, 1985.

Takai et al., 'Effective Methods of Carbonyl Methylenation Using CH$_2$I$_2$-Zn-Me$_3$Al and CH$_2$BR$_2$-Zn-TiCl$_4$ System', Tetrahedron Letters, No. 27, pp. 2417–2420, 1978.

Greene, T.W., "Protective Groups in Organic Synthesis", pp. 50–51, 1982.

*Primary Examiner*—C. Warren Ivy
*Assistant Examiner*—Lyman H. Smith
*Attorney, Agent, or Firm*—Cushman Darby & Cushman IP Group of Pillsbury Madison & Sutro, LLP

[57] ABSTRACT

The present invention provides a compound represented by the formula:

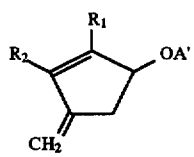

wherein R$_1$ denotes a hydrogen atom or a methyl group; R$_2$ represents a 1-methyl-2-propenyl group, a 1-methyl-2-propynyl group, a 3,3-dihalogeno-1-methyl-2-propenyl group or a C$_1$–C$_6$ alkyl group which may be substituted with at least one halogen atom; and A' represents a hydrogen atom or a protecting group for a hydroxyl group. The compound is useful in the preparation of esters which can be used to control insect pests.

6 Claims, No Drawings

ESTER COMPOUND, ACTIVE AGENT FOR CONTROLLING NOXIOUS INSECT PESTS CONTAINING THE SAME AS ACTIVE INGREDIENT, INTERMEDIATE FOR PRODUCTION OF THE ESTER COMPOUND AND PROCESS FOR PRODUCING THE INTERMEDIATE

This is a division of application Ser. No. 08/294,934, filed Aug. 23, 1994 now U.S. Pat. No. 5,550,258.

FIELD OF THE INVENTION

The present invention relates to an ester compound, an active agent for controlling noxious insect pests containing the ester compound as an active ingredient, an intermediate for production of the ester compound, and a process for producing the intermediate.

DESCRIPTION OF THE RELATED ART

Certain ester compounds have been disclosed as an active ingredient of pesticides, for example, in JAPANESE PATENT KOKAIs (Laid Open) No.S-56-75459 and No.S-57-67537. However, these ester compounds are not satisfactory for controlling noxious insect pests.

SUMMARY OF THE INVENTION

As a result of extensive study, the inventors have found that an ester compound represented by a formula I (shown below) having a unique alcohol moiety of the formula II is much more effective for controlling noxious insect pests. They also found useful processes which can provide said ester compound and said alcohol compound in good yields.

Thus the present invention provides an ester compound (hereinafter referred to as 'the present compound') represented by a formula I:

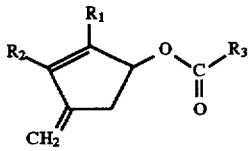

wherein $R_1$ denotes a hydrogen atom or a methyl group; $R_2$ represents a 1-methyl-2-propenyl group, a 1-methyl-2-propynyl group, a 3,3-dihalogeno-1-methyl-2-propenyl group, or a $C_1$–$C_6$ alkyl group which may be substituted with at least one halogen atom;

$R_3$ represents an acid residue of pyrethroids.

It also provides an pesticidal agent containing the same as an active ingredient for controlling noxious insect pests.

The present invention further provides an intermediate alcohol compound represented by the formula II:

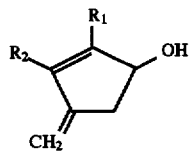

wherein $R_1$ and $R_2$ are the same as defined above, a process for producing the ester compound I and a process for producing the alcohol compound II.

PREFERRED EMBODIMENT OF THE INVENTION

The ester compound of the present invention shows good effect for controlling noxious insects, acarines or mites and nematodes.

First, description will be made on the ester compound represented by the formula I:

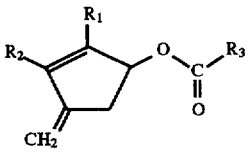

wherein $R_1$, $R_2$ and $R_3$ are the same as defined above.

Preferably 3,3-dihalogeno-1-methyl-2-propenyl group for $R_2$ is a 3,3-difluoro-1-methyl-2-propenyl group or a 3,3-dichloro-1-methyl-2-propenyl group.

Preferable $C_1$–$C_6$ alkyl groups which may be substituted with at least one halogen atom for $R_2$ include a 2,2,2-trifluoroethyl group, a 2,2-difluoroethyl group, a pentafluoroethyl group, a 2-fluoroethyl group, a 3-fluoropropyl group, a methyl group, an ethyl group, a n-propyl group, and an i-propyl group.

When the substituent $R_2$ of the present compound represents a $C_1$–$C_6$ alkyl group which may be substituted with at least one halogen atom, preferable examples of the $R_2$ are a $C_2$–$C_4$ alkyl group which may be substituted at least one fluorine atom such as a 2-fluoroethyl group, a 2,2,2-trifluoroethyl group or an ethyl group.

When the $C_1$–$C_6$ alkyl group which may be substituted with at least one halogen atom for $R_2$ is a methyl group, an ethyl group, n-propyl group, a 2-fluoroethyl group, a 2,2,2-trifluoroethyl group or a 3-fluoropropyl group, $R_1$ is preferably a methyl group.

When the substituent $R_2$ of the present compound represents a 1-methyl-2-propenyl group, a 1-methyl-2-propynyl group, a 3,3-dihalogeno-1-methyl-2-propenyl group or an isopropyl group, $R_1$ is preferably a hydrogen atom.

The acid residue of pyrethroids represented by $R_3$ (acid residue here means the group other than a carboxyl group of a carboxylic acid) may be any residue which can provide an active pyrethroid ester.

However, preferably $R_3$ is represented by a formula III:

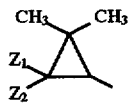

wherein $Z_1$ denotes a hydrogen atom or a methyl group; and $Z_2$ represents a hydrogen atom, a $C_1$–$C_6$ alkyl group, a $C_1$–$C_6$ alkoxy group, a ($C_1$–$C_6$ alkoxy)methyl group, a ($C_1$–$C_6$ alkoxy)ethyl group, a $C_2$–$C_4$ alkenyloxy group, a $C_2$–$C_4$ alkynyloxy group, a ($C_2$–$C_4$ alkenyl)oxymethyl group, or a ($C_2$–$C_4$ alkynyl)oxymethyl group, all of which except the hydrogen atom may be substituted with at least one halogen atom, $Z_2$ may alternatively represent a group of a formula IV:

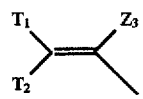

wherein $Z_3$ denotes a hydrogen atom or a halogen atom;

$T_1$ and $T_2$ may be the same or different, each denotes a hydrogen atom, a halogen atom, a cyano group, or a $C_1$–$C_3$ alkyl group or a phenyl group, the last two of which may be substituted with at least one halogen atom;

$T_1$ and $T_2$ may be combined with each other at their terminals to form a $C_3$–$C_6$ cycloalkyl group or a group represented by a formula V:

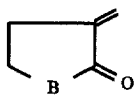

wherein B denotes an oxygen atom or a sulfur atom, or $Z_2$ can alternatively represent a group of a formula VI:

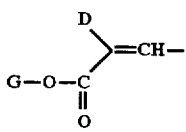

wherein D represents a hydrogen atom or a halogen atom; and

G denotes a $C_1$–$C_6$ alkyl group, a $C_3$–$C_5$ cycloalkyl group or a phenyl group, all of which may be substituted with at least one halogen atom.

Alternatively $R_3$ may be a group represented by a formula VII:

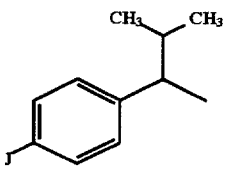

wherein J denotes a halogen atom or a $C_1$–$C_6$ alkyl group or a $C_1$–$C_6$ alkoxy group, the last two of which may be substituted with at least one halogen atom.

Preferable $Z_2$ group for the formula III includes a methyl group, an ethoxy group, a n-propoxy group, a n-butoxy group, an allyloxy group, a propargyloxy group, an allyoxymethyl group, a propargyloxymethyl group and a 2,2,2-trifluoroethoxy.

When $Z_2$ group represents the formula III, $Z_3$ is preferably a hydrogen atom; and $T_1$ and $T_2$ are same or different and each represents a methyl group, a chlorine atom, a bromine atom, a trifluoromethyl group, a fluorine atom, a p-chlorophenyl group or a cyano group.

When $Z_2$ group represents the formula VI, D represents preferably a hydrogen atom or a fluorine atom and G is preferably a 2-fluoroethyl group, a 1,1,1,3,3,3-hexafluoropropan-2-yl group, a 2,2,2-trifluoroethyl group, a methyl group or an ethyl group.

When $R_3$ represents the formula VII, preferably the substituent J is a fluorine atom, a chlorine atom, a trifluoromethyl group, a difluoromethyl group, trifluoromethoxy group or a difluoromethoxy group.

The halogen atom contained in the present compound includes a fluorine atom, a chlorine atom and a bromine atom.

The present compound can be produced by one of the following methods.

Method A:

A method of producing the present compound of the formula I which comprises reacting an alcohol compound represented by a formula II:

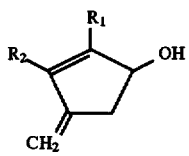

wherein $R_1$ and $R_2$ represent those specified above, with a carboxylic acid represented by a formula VIII:

$R_3$—COOH       VIII wherein $R_3$ denotes those specified above or a reactive derivative thereof.

Typical examples of the reactive derivative of the carboxylic acid include an acid halide and an acid anhydride.

The reaction can be conducted in an inert solvent in the presence of an appropriate condensing agent or base. The condensing agent to be used may be dicyclohexylcarbodiimide (DCC) or 1-ethyl-3-(3-diemthylaminopropyl) carbodiimide hydrochloride (WSC).

The base to be used may be an organic base such as triethylamine, pyridine, 4-dimethylaminopyridine, or diisopropylethylamine.

Typical examples of the inert solvent include hydrocarbons like benzene, toluene, and hexane; ethers like diethyl ether and tetrahydrofuran; and halogenated hydrocarbons such as dichloromethane and 1,2-dichloroethane.

A possible reaction temperature range is between $-20°$ C. and $100°$ C. or the boiling point of the solvent used for the reaction; or more preferably between $-5°$ C. and $100°$ C. or the boiling point of the solvent. The molar ratio of the alcohol compound represented by the formula II to the carboxylic acid represented by the formula XI or the reactive derivative thereof may be determined optionally, but is approximately one, preferably one. An equivalent to excess moles, or more specifically one to five moles, of the condensing agent or the base may be used according to the requirements to one mole of the alcohol compound represented by the formula II.

After completion of the reaction, the reaction solution is subjected to a conventional post-treatment such as solvent extraction and/or concentration to yield the present compound. The present compound obtained may be purified by column chromatography, distillation or recrystallization.

Method B:

A method of producing the present compound I which comprises reacting an ester derivative represented by a formula IX:

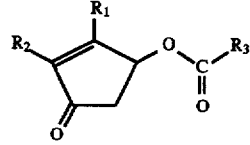

wherein $R_1$, $R_2$, and $R_3$ represent those specified above, in the presence of a base with a phosphonium salt represented by a formula X:

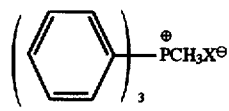

wherein X denotes a halogen atom such as a chlorine atom, a bromine atom or an iodine atom.

The reaction is usually conducted in an organic solvent, which may be an ether like diethyl ether, dimethoxyethane, or tetrahydrofuran or a hydrocarbon like hexane or toluene. A mixture of two or more organic solvents may be used.

Typical examples of the base to be used in the reaction include alkyllithiums such as n-butyllithium and methyllithium, and alkaline metal alkoxides (e.g. $C_1$–$C_4$ alkoxides such as potassium t-butoxide and sodium methoxide). A commercially available phosphonium salt (for example, methyltriphenyl phosphonium bromide by Aldrich Corp.) may be used as it is or purified if necessary.

The reaction temperature range is usually between –78° C. and 100° C. or the boiling point of the solvent used for the reaction, preferably between –78° C. and 30° C. One or two moles of the phosphonium salt represented by the formula X and one or two moles of the base are used to one mole of the ester derivative of the formula IX.

After completion of the reaction, the reaction solution is subjected to a conventional post-treatment such as solvent extraction and/or concentration to yield the present compound. The present compound obtained may be purified by column chromatography, distillation or recrystallization.

Method C:

A process for producing the present compound of the formula I which comprises reacting the ester derivative represented by the formula IX with a reaction mixture of (a) zinc (b) dibromomethane or diiodomethane and (c) titanium tetrachloride in an inert organic solvent.

The reaction is usually conducted in an inert organic solvent, which may be a halogenated hydrocarbon like dichloromethane or 1,2-dichloroethane, an ether like tetrahydrofuran, or a hydrocarbon like hexane or toluene. Two or more organic solvents may be mixed at an optional ratio if necessary.

A commercially available titanium tetrachloride (for example, the special grade by Kanto Chemical Corp.) may be used as it is or diluted with an organic solvent such as dichloromethane or toluene.

Usually 0.5 to 5 moles, preferably 0.9 to 1.2 moles of titanium tetrachloride is used to one mole of the ester derivative represented by the formula IX.

Zinc powder (zinc dust) is usually used for the reaction. Commercially available zinc dust (for example, zinc dust of approximately 325 mesh by Aldrich Corp.) may be used as it is or further activated according to a method specified in 'Reagents for Organic Synthesis', (Fieser et al., Vol. 1, p1276 (1967)).

Usually 2 to 50 moles, preferably 4 to 10 moles of zinc is used to one mole of the ester derivative of the formula IX.

The amount of dibromomethane or diiodomethane to be used to one mole of titanium tetrachloride is usually 1 to 10 moles, preferably 1 to 5 moles.

Titanium tetrachloride is usually added dropwise to a mixture of dibromomethane or diiodomethane and zinc in an inert organic solvent at a temperature of –40° C. to 50° C., preferably –20° C. to 5° C. After the reaction mixture is stirred at a temperature in these ranges, range, the ester derivative represented by the formula IX is added to the resultant reaction mixture and the mixture is usually further stirred at the temperature.

After completion of the reaction, sodium hydrogencarbonate and water are added to the reaction solution, and then filtered, the filtrate may subjected to a post-treatment such as solvent extraction or concentration to isolate the present compound. The reaction solution containing the compound may be used for a subsequent reaction process. The compound isolated may be purified by column chromatography or distillation if necessary.

The compound may have stereoisomers (R,S) or geometrical isomers (E,Z). The invention includes all the stereoisomers, geometrical isomers, and mixtures thereof having activities for controlling noxious organisms.

In the above methods A, B and C optically active compounds of the present invention may be obtained from optically active starting materials without causing racemization.

Next, description will be made on the intermediate alcohol compounds of the formula II used in the method A above. Typical examples of the alcohol compound include:

(RS)-3-ethyl-2-methyl-4-methylidene-2-cyclopentenol;

(1RS)-3-(1-methyl-2-propynyl)-4-methylidene-2-cyclopentenol;

(1RS)-3-(1-methyl-2-propenyl)-4-methylidene-2-cyclopentenol;

(1RS)-3-(1-methyl-(3,3-dichloro-2-propenyl))-4-methylidene-2-cyclopentenol;

(RS)-3-isopropyl-4-methylidene-2-cyclopentenol;

(RS)-3-(2,2,2-trifluoroethyl)-2-methyl-4-methylidene-2-cyclopentenol;

(RS)-3-(2-fluoroethyl)-2-methyl-4-methylidene-2-cyclopentenol;

(RS)-3-(3-fluoropropyl)-2-methyl-4-methylidene-2-cyclopentenol;

(S)-3-ethyl-2-methyl-4-methylidene-2-cyclopentenol;

(1S)-3-(1-methyl-2-propynyl)-4-methylidene-2-cyclopentenol;

(1S)-3-(1-methyl-2-propenyl)-4-methylidene-2-cyclopentenol;

(1RS)-3-(2,2,2-trifluoroethyl)-2-methyl-4-methylidene-2-cyclopentenol;

(S)-3-(2-fluoroethyl)-2-methyl-4-methylidene-2-cyclopentenol; and (S)-3-(3-fluoropropyl)-2-methyl-4-methylidene-2-cyclopentenol.

The alcohol compound of the formula II may be produced according to a method shown by a scheme I below:

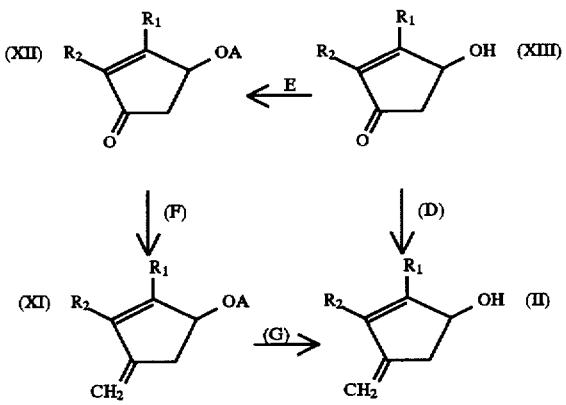

wherein $R_1$ and $R_2$ represent those specified above and A represents a protecting group for a hydroxyl group.

The protecting group A for a hydroxyl group may be any that does not adversely affect the reaction. Preferable examples of the protecting group A include: tri($C_1$–$C_6$) alkylsilyl groups such as a trimethylsilyl group, a triethylsilyl group and a t-butyldimethylsilyl group; 2-tetrahydrofuranyl group; 2-tetrahydropyranyl group; and a ($C_1$–$C_2$)alkyl group substituted with a ($C_1$–$C_2$)alkoxy group at the α-position such as a methoxymethyl group, a 1-methoxyethyl group, an ethoxymethyl group or a 1-ethoxyethyl group.

Examples of the alcohol derivative represented by the formula XI include:

(RS)-2-methyl-4-methylidene-3-ethyl-1-trimethylsilyloxy-2-cyclopentene;

(1RS)-4-methylidene-3-(1-methyl-2-propynyl)-1-trimethylsilyloxy-2-cyclopentene;

(1RS)-4-methylidene-3-(1-methyl-2-propenyl)-1-t-butyldimethylsilyloxy-2-cyclopentene;

(RS)-4-methylidene-3-isopropyl-1-triethylsilyloxy-2-cyclopentene;

(RS)-2-methyl-4-methylidene-3-(2,2,2-trifluoroethyl)-1-triisopropylsilyloxy-2-cyclopentene;

(RS)-2-methyl-4-methylidene-3-(2-fluoroethyl)-1-t-butyldimethylsilyloxy-2-cyclopentene;

(RS)-2-methyl-4-methylidene-3-(3-fluoropropyl)-1-triethylsilyloxy-2-cyclopentene;

(RS)-2-methyl-4-methylidene-3-ethyl-1-methoxymethyloxy-2-cyclopentene;

(S)-4-methylidene-3-(1-methyl-2-propynyl)-1-(2-tetrahydropyranyl)oxy-2-cyclopentene; and (RS)-4-methylidene-3-(1-methyl-2-propenyl)-1-ethoxyethyloxy-2-cyclopentene.

In the scheme I, the compound of the formula XIII can be produced, for example, by a method disclosed in JAPANESE PATENT KOKAI (Laid Open) No.S-57-67537.

The process D for directly producing the alcohol compound represented by the formula II from the compound of the formula XIII is conducted by the method B described above.

Namely, the alcohol compound of the formula II produced by using the compound XIII as a starting material in place of the ester derivative of the formula IX.

The process E for protecting a hydroxyl group of the cyclopentenolone compound XIII to produce the compound XII is conducted according to a method specified in 'Protective Group in Organic Synthesis' (T. W. Greene and P. G. M. Wuts; 2nd edition, John Wiley & Sons, Inc. pages 10–86, (1991)).

However, preferably the process is conducted by one of the following methods (i) to (iii).

(i) When A represents tri($C_1$–$C_6$)alkylsilyl group;

The protecting of the hydroxy group of the cyclopentenolone compound XIII is carried out by reacting a tri ($C_1$–$C_6$)alkylsilyl chloride or tri($C_1$–$C_6$)alkylsilyl triflate with the cyclopentenolone compound XIII in the presence of a base.

The reaction is usually conducted in an inert organic solvent. Examples of the solvent are a halogenated hydrocarbon solvent like dichloromethane, an ether solvent like tetrahydrofuran or diethyl ether or a polar aprotic solvent like N,N-dimethylformamide.

1 to 10 moles, preferably 1.2 to 5 moles of an organic base like imidazole, triethylamine, diisopropylethylamine, pyridine or 2,6-dimethylpyridine and 1 to 2 moles, preferably 1 to 1.5 moles of tri($C_1$–$C_6$)alkylsilyl chloride or tri($C_1$–$C_6$) alkylsilyl triflate are used to 1 mole of the cyclopentenolone compound.

The reaction temperatures is usually –30° C. to 50° C., preferably –10° C. to 30° C.

ii) When A represents 2-tetrahydrofuranyl group or 2-tetrahydropyranyl group;

The protecting of the hydroxy group of the cyclopentenolone compound XIII is carried out by reacting dihydropyran or dihydrofuran with the cyclopentenolone compound XIII in the presence of an acid.

The reaction may be conducted in an aprotic organic solvent such as an ether solvent like diethyl ether or tetrahydrofuran, a hydrocarbon solvent like benzene or toluene, or a halogenated hydrocarbon solvent like dichloromethane or chloroform.

1 to 50 moles, preferably 1 to 10 moles of dihydropyran or dihydrofuran are allowed to react with the compound XIII in the presence of a catalytic amount of an acid such as organic acid (e.g. p-toluenesulfonic acid or pyridine p-toluenesulfonate) or an inorganic acid, such as phosphoric acid, hydrochloric acid, or sulfuric acid at 0° C. to 30° C. or at an ambient temperature.

(iii) When A represents a ($C_1$–$C_2$)alkyl group substituted with a ($C_1$–$C_2$)alkoxy group at the α-position;

The protecting of the hydroxy group of the cyclopentenolone compound is carried out by reacting a ($C_1$–$C_2$)alkyl chloride group substituted with a ($C_1$–$C_2$)alkoxy group at the α-position with the cyclopentenolone compound XIII in the presence of a base.

Examples of the solvent to be used are a halogenated hydrocarbon solvent like dichloromethane or chloroform, an ether solvent like diethyl ether or tetrahydrofuran, or a hydrocarbon solvent like benzene or toluene.

1 to 10 moles, preferably 1 to 5 moles of an organic base like triethylamine, diisopropylethylamine, or 2,6-diemthylpyridine or an alkaline metal hydride like sodium hydride or potassium hydride and 1 to 50 moles, preferably 1 to 5 moles of a ($C_1$–$C_2$)alkyl chloride substituted with a ($C_1$–$C_2$)alkoxy group at the α-position are allowed to react with the compound at a temperature of –20° C. to 50° C., preferably 0° C. to 20° C.

The process F for preparing the compound IX from the compound XII is conducted according to the method C described above using the compound XII as a starting material in place of the ester derivative of the formula IX.

The compound XI may be produced according to the method B described above using the compound XII as a starting material in place of the ester derivative of the formula IX.

The process G for producing the alcohol compound of the formula II from the compound XI is conducted according to a method specified in 'Protective Group in Organic Synthesis' (T. W. Greene and P. G. M. Wuts; 2nd edition, John Wiley & Sons, Inc. pp10–86, (1991)).

However, preferably the process is carried out by one of the following methods (i) to (iii).

(i) When A represents tri($C_1$–$C_6$)alkylsilyl group;

The removing of the protecting group is carried out by contacting the alcohol derivative of the formula III with an acid or a fluoride anion.

Examples of an acid are: an ether solvent like tetrahydrofuran or diethyl ether, a halogenated hydrocarbon solvent like dichloromethane, a hydrocarbon solvent like benzene or toluene, or a protic solvent like water, methanol, or ethanol, an inorganic acid like hydrochloric acid, or sulfuric acid, or an organic acid such as formic acid or acetic acid, which may be mixed with water if necessary.

Examples of a fluoride anion are tetrabutylammonium fluoride and hydrofluoric acid.

The reaction temperature is usually 0° C. to 30° C.

(ii) When A represents 2-tetrahydrofuranyl group or 2-tetrahydropyranyl group;

The removing of the protecting group is carried out by contacting the alcohol derivative of the formula III with a catalytic to excess amount of an acid (an organic acid like p-toluenesulfonic acid or a salt thereof, or an inorganic acid like hydrochloric acid or sulfuric acid).

The reaction is usually conducted in a protic solvent, such as water, methanol, or ethanol, or a mixed solvent of the protic solvent and an ether solvent, such as diethyl ether or tetrahydrofuran.

The reaction temperature is usually 0° C. to 50° C.

(iii) When A represents a ($C_1$–$C_2$)alkyl group substituted with a ($C_1$–$C_2$)alkoxy group at the α-position;

The removing of the protecting group is carried out by contacting the alcohol derivative XI with a catalytic to excess amount of an acid such as an organic acid like formic acid, acetic acid, or methanesulfonic acid or an inorganic acid like hydrochloric acid or sulfuric acid.

The reaction is usually conducted in a protic solvent, such as water, methanol or ethanol, or a mixed solvent of the protic solvent and an ether solvent such as diethyl ether or tetrahydrofuran.

The reaction temperature is usually 20° C. to the refluxing temperature of the solvent.

In the above method (i), (ii) or (iii) the alcohol derivative XI obtained in a solution form by usual post-treatment after the olefination process can be used as it is without isolating.

The ester derivative of the formula IX used as a starting material in the method B and the method C may be prepared, for example, according to a method disclosed in JAPANESE PATENT KOKAI (Laid Open No.S-56-75459 and No. S-57-67537.

Preferable examples of the present ester compounds are shown in the Table 1 below.

TABLE 1

| Compound No. | $R_1$ | $R_2$ | Notation of stereoisomerism of the alcohol moiety | $R_3$ | Notation of the stereoisomerism of the carboxylic acid moiety | Physical constant (Refractive Index) $n_D$ (°C.) |
|---|---|---|---|---|---|---|
| 1 | $CH_3$ | $C_2H_5$— | (RS) | (structure with $CH_3$, $CH_3$ cyclopropyl and =C(CH$_3$)$_2$) | (1R)-trans | 1.5070 (20.5) |
| 2 | H | $CH_2$=CH—CH($CH_3$)— | (RS) | (cyclopropyl with =C(CH$_3$)$_2$) | (1R)-cis, trans | 1.5076 (23) |
| 3 | H | CH≡C—CH($CH_3$)— | (RS) | (cyclopropyl with =C(CH$_3$)$_2$) | (1R)-trans | |
| 4 | H | $CH_2$=CH—CH($CH_3$)— | (RS) | (cyclopropyl with =CCl$_2$) | (1R)-trans | 1.5251 (24.5) |
| 5 | $CH_3$ | $C_2H_5$ | (RS) | (cyclopropyl with =CCl$_2$) | (1R)-trans | 1.5251 (23) |
| 6 | H | $CH_3$—CH($CH_3$)— | (RS) | (cyclopropyl with =C(CF$_3$)Cl) | (1RS)-cis (Z) | 1.4804 (26) |
| 7 | H | $CH_2$=CH—CH($CH_3$)— | (RS) | (cyclopropyl with —CH—OC$_2$H$_5$) | (1RS)-cis, trans | |

TABLE 1-continued

| Compound No. | R₁ | R₂ | Notation of stereoisomerism of the alcohol moiety | R₃ | Notation of the stereoisomerism of the carboxylic acid moiety | Physical constant (Refractive Index) $n_D$ (°C.) |
|---|---|---|---|---|---|---|
| 8 | H | CH₂=CH—CH(CH₃)— | (RS) | 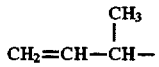 | (1R)-trans | 1.5902 (25) |
| 9 | CH₃ | C₂H₅— | (RS) | 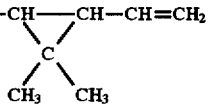 | — | 1.4991 (23.5) |
| 10 | CH₃ | C₂H₅— | (RS) | 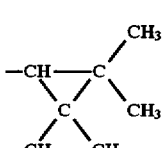 | (1RS)-trans | 1.4848 (25) |
| 11 | H | CH₃—CH(CH₃)— | (RS) | 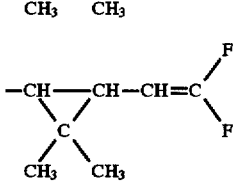 | (1R)-trans | 1.5197 (25) |
| 12 | H | CH₂=CH—CH(CH₃)— | (RS) | 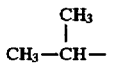 | — | 1.5023 (23) |
| 13 | H | CH₂=CH—CH(CH₃)— | (RS) | 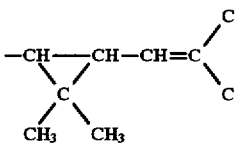 | (1R)-trans | |
| 14 | CH₃ | CH₃— | (RS) | 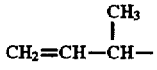 | (1RS)-trans | 1.4883 (25) |
| 15 | CH₃ | CF₃CH₂— | (RS) | 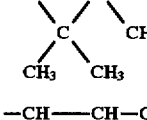 | (1R)-trans | 1.4805 (21) |
| 16 | H | CH₂=CH—CH(CH₃)— | (RS) | 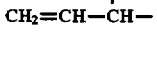 | (S) | |
| 17 | H | CH₃CH(CH₃)— | (RS) | 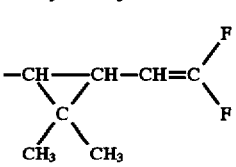 | (1R)-trans (EZ) | 1.5014 (23.5) |

TABLE 1-continued

| Compound No. | R₁ | R₂ | Notation of stereoisomerism of the alcohol moiety | R₃ | Notation of the stereoisomerism of the carboxylic acid moiety | Physical constant (Refractive Index) $n_D$ (°C.) |
|---|---|---|---|---|---|---|
| 18 | H | CH₂=CH—CH(CH₃)— | (RS) | 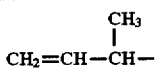 | (1R)-trans | |
| 19 | CH₃ | C₂H₅— | (RS) | 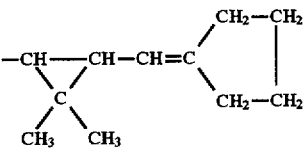 | (1R)-trans | 1.5061 (24) |
| 20 | CH₃ | C₂H₅— | (RS) | 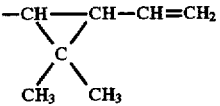 | (1R)-cis | 1.5102 (22.5) |
| 21 | CH₃ | C₂H₅— | (RS) | 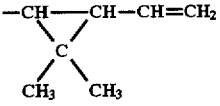 | (1R)-cis, trans | 1.5070 (23.5) |
| 22 | H | CH₃—CH(CH₃)— | (RS) | 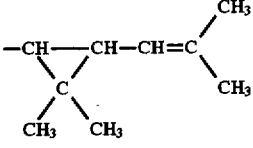 | (1RS)-trans | 1.4797 (25) |
| 23 | H | CF₂=CH—CH(CH₃)— | (RS) | 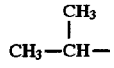 | (1R)-trans | |
| 24 | CH₃ | C₂H₅— | (RS) | 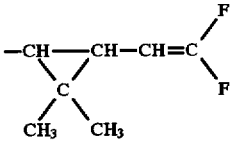 | (1R)-trans | 1.4930 (23.5) |
| 25 | H | CH₂=CH—CH(CH₃)— | (RS) | 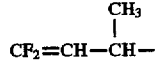 | (1R)-cis (E) | |
| 26 | H | CH₂=CH—CH(CH₃)— | (RS) | 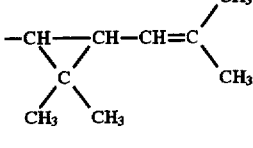 | (1R)-trans | |
| 27 | H | CH₃—CH(CH₃)— | (RS) | 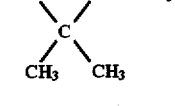 | — | 1.4917 (26.5) |

TABLE 1-continued

| Compound No. | $R_1$ | $R_2$ | Notation of stereoisomerism of the alcohol moiety | $R_3$ | Notation of the stereoisomerism of the carboxylic acid moiety | Physical constant (Refractive Index) $n_D$ (°C.) |
|---|---|---|---|---|---|---|
| 28 | $CH_3$ | $C_2H_5-$ | (RS) | cyclopropyl(gem-diCH$_3$)–CH–CH=C with thiolactone ring (–CH$_2$–CH$_2$–C(=O)–S–) | (1R)-cis (E) | |
| 29 | $CH_3$ | $C_2H_5-$ | (RS) | cyclopropyl(gem-diCH$_3$)–CH–CH=CFCl | (1R)-trans (E/Z) | 1.5045 (25) |
| 30 | $CH_3$ | $n-C_3H_7-$ | (RS) | cyclopropyl(gem-diCH$_3$)–CH–CH$_2$OCH$_2$C≡CH | (1R)-trans | |
| 31 | H | $CH≡C-CH(CH_3)-$ | (RS) | cyclopropyl(gem-diCH$_3$)–CH–CH=C(F)(COOC$_2$H$_5$) | (1R)-cis (E) | |
| 32 | H | $CH_3-CH(CH_3)-$ | (RS) | cyclopropyl(gem-diCH$_3$)–CH–CH=C(CH$_3$)$_2$ | (1R)-cis, trans | 1.4995 (27.0) |
| 33 | $CH_3$ | $CF_3CH_2-$ | (RS) | cyclopropyl(gem-diCH$_3$)–CH–CH=CCl$_2$ | (1RS)-trans | |
| 34 | H | $CH_2=CH-CH(CH_3)-$ | (RS) | cyclopropyl(gem-diCH$_3$)–CH–CH=CClF | (1R)-trans (E/Z) | 1.5047 (24.5) |
| 35 | H | $CH_2=CH-CH(CH_3)-$ | (RS) | cyclopropyl(gem-diCH$_3$)–CH–OCH$_2$CF$_3$ | (1RS)-cis, trans | |
| 36 | H | $Cl_2C=CH-C(CH_3)-$ | (RS) | cyclopropyl(gem-diCH$_3$)–CH–CH=CCl$_2$ | (1R)-trans | |
| 37 | $CH_3$ | $CH_3-$ | (RS) | cyclopropyl(gem-diCH$_3$)–CH–CH=C(CH$_3$)$_2$ | (1R)-cis, trans | 1.5098 (22) |

TABLE 1-continued

| Compound No. | R₁ | R₂ | Notation of stereoisomerism of the alcohol moiety | R₃ | Notation of the stereoisomerism of the carboxylic acid moiety | Physical constant (Refractive Index) $n_D$ (°C.) |
|---|---|---|---|---|---|---|
| 38 | CH₃ | C₂H₅— | (RS) | ![structure: cyclopropyl with CH₃, CH₃, CH₂] | (1R) | |
| 39 | H | CH₂=CH—CH(CH₃)— | (RS) | cyclopropyl —CH—CH=C(COOCH₃)(CH₃) with gem-dimethyl | (1R)-cis (E) | |
| 40 | H | CH≡C—CH(CH₃)— | (RS) | cyclopropyl —CH—CH=C(F)(CN) with gem-dimethyl | (1R)-cis (E) | |
| 41 | H | CH≡C—CH(CH₃)— | (RS) | cyclopropyl —CH—CH=C(Cl)(4-Cl-C₆H₄) with gem-dimethyl | (1R)-trans (Z) | |
| 42 | H | CH≡C—CH(CH₃)— | (RS) | cyclopropyl —CH—CH=C with lactone (C(=O)—O—CH₂—CH₂) | (1R)-cis (E) | |
| 43 | CH₃ | CF₃CH₂— | (RS) | cyclopropyl —CH—C(CH₃)₂ with gem-dimethyl | — | 1.4687 (24) |
| 44 | CH₃ | CH₃— | (RS) | cyclopropyl —CH—C(CH₃)₂ with gem-dimethyl | — | 1.4980 (22) |
| 45 | CH₃ | C₂H₅— | (RS) | cyclopropyl —CH—CH=C(CF₃)(Cl) with gem-dimethyl | (1RS)-cis (E) | 1.4969 (23.5) |
| 46 | H | HC≡C—CH(CH₃)— | (RS) | cyclopropyl —CH—CH=C(Cl)₂ with gem-dimethyl | (1R)-trans | |

TABLE 1-continued

| Compound No. | R₁ | R₂ | Notation of stereoisomerism of the alcohol moiety | R₃ | Notation of the stereoisomerism of the carboxylic acid moiety | Physical constant (Refractive Index) $n_D$ (°C.) |
|---|---|---|---|---|---|---|
| 47 | H | HC≡C-CH(CH₃)- | (RS) | cyclopropyl-CH=C(CH₃)(CH₃) with gem-dimethyl | — | |
| 48 | H | HC≡C-CH(CH₃)- | (RS) | cyclopropyl-CH=C(CF₃)(Cl) with gem-dimethyl | (1RS)-cis (Z) | |
| 49 | H | HC≡C-CH(CH₃)- | (RS) | cyclopropyl-CH=CH-CH₃ with gem-dimethyl | (1R)-trans | |
| 50 | CH₃ | FCH₂CH₂CH₂— | (RS) | cyclopropyl-CH=C(CH₃)₂ with gem-dimethyl | (1R)-trans | |
| 51 | CH₃ | FCH₂CH₂— | (RS) | cyclopropyl-CH=C(CH₃)₂ with gem-dimethyl | (1R)-trans | |
| 52 | CH₃ | FCH₂CH₂CH₂— | (RS) | cyclopropyl-C(CH₃)(CH₃) with gem-dimethyl | — | |
| 53 | CH₃ | FCH₂CH₂— | (RS) | cyclopropyl-C(CH₃)(CH₃) with gem-dimethyl | — | |
| 54 | CH₃ | CF₃CH₂— | (RS) | cyclopropyl-CH=CCl₂ with gem-dimethyl | (1R)-trans | 1.4999 (21) |

TABLE 1-continued

| Compound No. | $R_1$ | $R_2$ | Notation of stereoisomerism of the alcohol moiety | $R_3$ | Notation of the stereoisomerism of the carboxylic acid moiety | Physical constant (Refractive Index) $n_D$ (°C.) |
|---|---|---|---|---|---|---|
| 55 | H | CH₃-CH-C≡CH (with CH₃) | (RS) | cyclopropyl-CH=CF₂ with gem-diCH₃ | (1R)-trans | |
| 56 | H | CH₃-CH-C≡CH | (RS) | cyclopropyl-CH=CClF with gem-diCH₃ | (1R)-trans (E/Z) | |
| 57 | H | HC=CH-CH(CH₃) | (RS) | cyclopropyl-CH=CF₂ with gem-diCH₃ | (1R)-trans | |
| 58 | H | CH₃-CH-C≡CH | (RS) | cyclopropyl-CH=CH₂ with gem-diCH₃ | (1R)-trans | |
| 59 | CH₃ | CF₃CH₂— | (RS) | cyclopropyl-CH(CH₃) with gem-diCH₃ | (1R)-trans | |
| 60 | CH₃ | CH₃CH₂CH₂— | (RS) | cyclopropyl-CH=C(CH₃)₂ with gem-diCH₃ | (1R)-trans | |
| 61 | CH₃ | CH₃CH₂CH₂— | (RS) | cyclopropyl-C(CH₃)₂ with gem-diCH₃ | — | |
| 62 | H | CF₂=CH-CH(CH₃) | (RS) | cyclopropyl-CH=CCl₂ with gem-diCH₃ | (1R)-trans | |

TABLE 1-continued

| Compound No. | R₁ | R₂ | Notation of stereoisomerism of the alcohol moiety | R₃ | Notation of the stereoisomerism of the carboxylic acid moiety | Physical constant (Refractive Index) $n_D$ (°C.) |
|---|---|---|---|---|---|---|
| 63 | H | $\underset{HC\equiv C}{\overset{CH_3}{\underset{|}{CH}}}-$ | (RS) | cyclopropyl-CH=CBr₂ (2,2-dimethyl) | (1R)-cis | |
| 64 | H | $\underset{HC\equiv C}{\overset{CH_3}{\underset{|}{CH}}}-$ | (RS) | cyclopropyl-CH=CHCH₃ (2,2-dimethyl) | (1R)-trans (E/Z) | |
| 65 | H | $\underset{HC\equiv C}{\overset{CH_3}{\underset{|}{CH}}}-$ | (RS) | cyclopropyl-CH=C(COO-CH(CF₃)₂) (2,2-dimethyl) | (1R)-cis (Z) | |
| 66 | H | $\underset{HC\equiv C}{\overset{CH_3}{\underset{|}{CH}}}-$ | (RS) | cyclopropyl-CH=CH₂ (2,2-dimethyl) | (1R)-trans | |
| 67 | CH₃ | CF₃CH₂— | (RS) | cyclopropyl-C(F)=CH-COOC₂H₅ | (1R)-cis (E) | |
| 68 | CH₃ | CF₃CH₂— | (RS) | cyclopropyl-C(F)=CH-COOC₂H₅ | (1R)-trans (E) | |
| 69 | CH₃ | CF₃CH₂— | (RS) | cyclopropyl-C(F)=CH-COOCH₃ | (1R)-trans (E) | |
| 70 | CH₃ | CF₃CH₂— | (RS) | cyclopropyl-CH=C(CH₃)-COOCH₃ | (1R)-trans (E) | 1.4940 (22) |
| 71 | CH₃ | CF₃CH₂— | (RS) | cyclopropyl-CH=CBr₂ | (1R)-cis | |

TABLE 1-continued

| Compound No. | $R_1$ | $R_2$ | Notation of stereoisomerism of the alcohol moiety | $R_3$ | Notation of the stereoisomerism of the carboxylic acid moiety | Physical constant (Refractive Index) $n_D$ (°C.) |
|---|---|---|---|---|---|---|
| 72 | $CH_3$ | $CF_3CH_2-$ | (RS) | 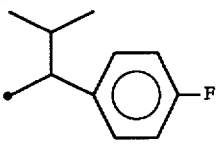 | (S) | 1.4879 (23) |
| 73 | $CH_3$ | $CF_3CH_2-$ | (RS) | 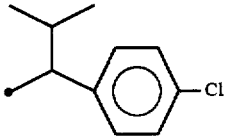 | (S) | |
| 74 | $CH_3$ | $CF_3CH_2-$ | (RS) | 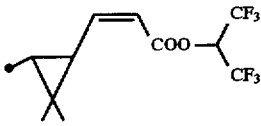 | (1R)-cis (Z) | |
| 75 | $CH_3$ | $F_2CHCH_2-$ | (RS) |  | | |
| 76 | $CH_3$ | $FCH_2CH_2-$ | (RS) |  | | |
| 77 | $CH_3$ | $CF_3CF_2-$ | (RS) | 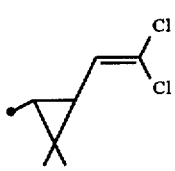 | (1R)-trans | |
| 78 | $CH_3$ | $FCH_2CH_2-$ | (RS) | 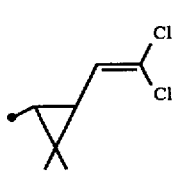 | (1R)-trans | |
| 79 | $CH_3$ | $F_2CHCH_2-$ | (RS) | 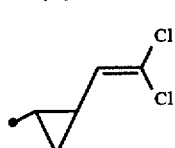 | (1R)-trans | |
| 80 | $CH_3$ | $FCH_2CH_2CH_2-$ | (RS) | 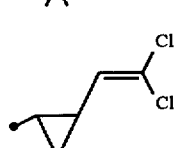 | (1R)-trans | |
| 81 | $CH_3$ | $CF_3CH_2-$ | (RS) | 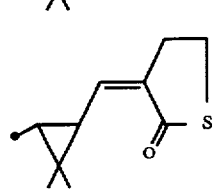 | (1R)-cis (E) | |

TABLE 1-continued

| Compound No. | R₁ | R₂ | Notation of stereoisomerism of the alcohol moiety | R₃ | Notation of the stereoisomerism of the carboxylic acid moiety | Physical constant (Refractive Index) $n_D$ (°C.) |
|---|---|---|---|---|---|---|
| 82 | CH₃ | CF₃CH₂— | (RS) | | (1R)-trans | |
| 83 | CH₃ | CF₃CH₂— | (RS) | | (1RS)-trans | |
| 84 | CH₃ | CF₃CH₂— | (RS) | | (1RS)-cis (Z) | |
| 85 | CH₃ | CF₃CF₂— | (RS) | | (1R)-cis (Z) | |
| 86 | CH₃ | CF₃CH₂— | (RS) | | (1R)-trans | |
| 87 | CH₃ | CF₃CH₂— | (RS) | | (1R)-trans (E/Z) | |
| 88 | CH₃ | FCH₂CH₂— | (RS) | | (1R)-trans (E/Z) | |
| 89 | CH₃ | CF₃CF₂— | (RS) | | (1R)-trans | |
| 90 | CH₃ | F₂CHCH₂— | (RS) | | (1R)-trans | |

The compound of the present invention is effective for controlling noxious insects, mites and nematodes listed below:

Hemiptera:
Delphacidae (leaf hoppers) such as *Laodelphax striatellus*, *Nilparvate lugens* and *Sogatella furcifera*; Cicadelloidea (leaf hoppers) such as *Nephotettix cincticeps* and *Nephotettix virescens*, Aphididea (aphids), Pentatomidae (stink bugs), Aleyrodidae, Coccoidea (scale insects), Tingidae (lacebugs), Psyllidae (jumping plant-lices), etc.;

Lepidoptera:

Pyralidae such as *Chilo suppressalis* and *Cnaphalocrocis medinalis*, Noctuidae (owlet moths) such as *Spodoptera litura*, *Pseudaletia separata*, and *Mamestra brassicae*, Heliothis moths, Agrotis moths like *Agrotis ipsilon* and *Agrotis segetum* (turnip moth), Pieridae such as *Pieris rapae crucivora*, Tortricidae (bell moths), Lyonetiidae (leaf mining moths), *Euproctis subflava*, *Plutella xylostella*, *Tinea translucens*, *Tineola bisselliella*, etc.;

Diptera:

Culex (house mosquitos) such as *Culex pipiens pallens* and *Cules tritaeniorhynvchus*, Aedes such as *Aedes albopictus* and *Aedes aegypti*, Anophelinae such as *Anophelinae sinensis*, Chironomidae (midges), Muscidae such as *Musca domestica* (house fly) and *Muscina stabulans*, Calliphoridae (blow flies), Sarcophagidae (flesh flies), Anthomyiidae such as *Delia platura* and *Delia antigua*, Trypetidae (fruit flies), Drosophilidae (wine flies), Psychodidae (moth flies), Tabanidae (deer flies), Simuliidae (black flies), Stomoxyinae, etc.;

Coleoptera (beetles):

Diabrotica (corn rootworms) such as *Diabrotica virgifera* and *Diabrotica undecimunctata*, Scarabaeidae such as *Anomala cuprea* and *Anomala rufocuprea*, Curculionidae (snout beetles) such as *Sitophilus zeamais* (grain weevils) and *Lissorphoptrus oryzophilus*, darkling beetles such as *Neatus ventralis*, *Tenebrio molitor* and *Tribolium castaneum*, Chrysomelidae (leaf beetles) such as *Aulacophora femoralis* and *Phyllotreta striolata*, Anobiidae (death-watch beetles), Epilachna such as *Henosepilachna vigintioctopunctata*, Lyctidae (powder-post beetles), Bostrychidae (lesser grain borers), *Paederus fuscipes*, etc.;

Blattaria (cockroaches):

*Blattella germanica*, *Periplaneta fuliginosa*, *Periplaneta americana*, *Periplaneta brunnea*, *Blatta orientalis*, etc.;

Thysanoptera (thrips):

*Thrips palmi*, *Thrips hawaiiensis*, etc.;

Hymenoptera:

Formicidae (ants), Vespa (hornets), Bethylidae (bethylid wasps), Tenthredinidae (sawflies) like *Athalia japonica* (cabbage sawfly), etc.;

Orthoptera:

Gryllotalpa (mole crickets), Acrididea (grasshoppers), etc.;

Siphonaptera (fleas):

*Purex irritans*, etc.;

Anoplura (sucking louses):

*Pediculus humanus*, *Phthirus pubis*, etc.;

Isoptera (termites):

*Reticulitermes speratus*, *Coptotermes formosanus*, etc.;

Tetranychidae (spider mites):

*Tetranychus cinnabarinus*, *Tetranychus urticae*, *Tetranychus kanzawai*, *Panonychus citri*, *Panonychus ulmi*, etc.;

Ixodidae (ticks):

*Boophilus microplus;* house dust mites:

Acaridae, Pyroglyphidae, Cheyletidae, *Ornithonyssus bacoti*, etc.;

Nematoda (soil nematodes):

root-lesion nematodes, cyst nematodes, root-knot nematodes, etc.; and

Nematoda (nematodes):

*Bursaphelenchus xylophilus* (pine wood nematodes), etc.

The present compound to be used as an active ingredient of an insecticide, an acaricide, a nematicide or an active agent for controlling soil insect pests is usually formulated by mixing with a solid carrier, a liquid carrier, a gaseous carrier or bait, or is supported by a base material of a mosquito-coil or mosquito-mat for electric heating fumigation through impregnation.

A surfactant, a sticking agent, a dispersion agent, a stabilizer and other auxiliaries or additives are added if necessary.

Examples of the formulations for the present compound include oil solutions, emulsifiable concentrates, wettable powders, flowables such as water suspensions and emulsions, granules, dusts, aerosols, combustible or chemical fumigants such as mosquito-coil, mosquito-mats for electric heating fumigation and a porous ceramic fumigant, volatile agents applied on resin or paper, fogging agents, ULV agents (formulations for ultra low volume application) and poisonous bait.

These formulations usually include the present compound as an active ingredient in an amount of 0.001% to 95% by weight.

Examples of the solid carrier to be used for the formulations include fine powder or granules of clays (e.g. kaolin clay, diatomaceous earth, synthetic hydrated silicon oxide, bentonite, Fubasami clay and acid clay), talcs, ceramics, other inorganic minerals (e.g. sericite, quartz, sulfur, active carbon, calcium carbocarbonate and hydrated silica) and chemical fertilizers (e.g. ammonium sulfate, ammonium phosphate, ammonium nitrate, urea and ammonium chloride).

Examples of the liquid carrier include water, alcohols such as methanol and ethanol, ketones such as acetone and methylethyl ketone, aromatic hydrocarbons such as benzene, toluene, xylene, ethylbenzene, and methylnaphthalene, aliphatic hydrocarbons such as hexane, cyclohexane, kerosine, and gas oil, esters such as ethyl acetate and butyl acetate, nitriles such as acetonitrile and isobutyronitrile, ethers such as diisopropyl ether and dioxane, acid amides such as N,N-dimethylformamide and N,N-dimethylacetoamide, halogenated hydrocarbons such as dichloromethane, trichloroethane, and carbon tetrachloride, dimethyl sulfoxide, vegetable oils such as soybean oil and cottonseed oil.

Examples of the gaseous carrier or propellant include CFCs (chlorofluorocarbons), butane gas, LPG (liquefied petroleum gas), dimethyl ether and carbon dioxide.

Examples of the surfactant includes alkyl sulfates, alkyl sulfonates, aralkyl sulfonates, aralkyl ethers, poly(ethylene glycol)s, polyethylene glycol ethers, polyhydric alcohol derivatives, and sugar alcohol derivatives.

Examples of the sticking agent, the dispersing agent and other equivalent additives or auxiliaries include casein, gelatin, polysaccharides such as starch, gum arabic, cellulose derivatives and alginic acid, lignin derivatives, bentonite, sugars and synthetic water-soluble polymers such as polyvinyl alcohol, polyvinyl pyrrolidone and polyacrylic acid.

Examples of the stabilizer include PAP (acid isopropyl phosphate), BHT (2,6-di-t-butyl-4-methyl-phenol), BHA (mixture of 2-t-butyl-4-methoxyphenol and 3-t-butyl-4-methoxyphenol), vegentable oils, mineral oils, surfactants, fatty acides and esters of fatty acids.

The base material of the mosquito-coil may be a mixture of raw plant powder such as wood powder and lees powder, powder of *Machilus thunbergii* Sieb. et Zucc., and a binding agent like starch or gluten.

The base material of mosquito-mat for electric heating fumigation may be a plate of compacted fibrils of cotton linters or a mixture of pulp and cotton linters.

The base material of the combustible fumigant includes, for example, an exothermic agent such as a nitrate, a nitrite, a guanidine salt, potassium chlorate, nitrocellulose, ethylcellulose or wood powder, a pyrolytic stimulating agent such as an alkaline metal salt, an alkaline earth metal salt, a dichromate or a chromate, an oxygen source such as potassium nitrates, a combustion assistant such as melamine or wheat starch, a bulk filler such as diatomaceous earth and a binding agent such as synthetic glue.

The base material of the chemical fumigant includes, for example, an exothermic agent such as an alkaline metal sulfide, a polysulfide, a hydrosulfide, a hydrated salt or calcium oxide, a catalytic agent such as a carbonaneous substance, iron carbide or activated clay, an organic foaming agent such as azodicarbonamide, benzenesulfonylhydrazide, N,N'-dinitrosopentamethylene, tetramine, polystyrene or polyurethane and a filler such as natural or synthetic fibers.

Examples of the base material of the volatile agent include thermoplastic resins, filter paper and rice paper.

The base material of the poisonous baits includes a bait component such as grain powder, purified vegetable oil, sugar, or crystalline cellulose, an antioxidant such as dibutylhydroxytoluene or nordihydroguaiaretic acid, a preservative such as dehydroacetic acid, a substance for preventing erroneous eating such as red pepper powder, an attractant such as cheese flavor, onion flavor or peanut oil.

The flowables (water suspensions and emulsions) are usually prepared by finely dispersing the present compound at a ratio of 1 to 75% in water containing a 0.5 to 15% dispersing agent, a 0.1 to 10% suspension assistant (for example, protective colloid or a compound giving thixotropy) and 0 to 10% additives (for example, an antifoamer, a stabilizer, a bactericide, a rust preventive agent, an antimold, a developing agent, a penetrating assistant and an antifreezing agent).

The present compound may be dispersed in oil, in which the present compound is substantially insoluble, to form oil suspensions.

Examples of the protective colloid include casein, gelatin, gums, cellulose ethers and polyvinyl alcohol. The compound giving thixotropy may be bentonite, aluminum magnesium silicate, xanthan gum or polyacrylic acid.

The formulations thus obtained is used as prepared or diluted with water and may be used simultaneously with another insecticide, another acaricide, another nematicide, another soil insect controlling agent, a bactericide, a herbicide, a plant growth regulator, a synergist, a fertilizer or a soil conditioner under non-mixed conditions or pre-mixed conditions.

Insecticides, acaricides and nematocides to be used together with the present compounds include organophosphorous compounds such as Fenitrothion [(O,O-dimethyl O-(3-methyl-4-nitrophenyl) phosphorothionate],
Fenthion [O,O-dimethyl O-(3-methl-4-methylthiophenyl) phophorothionate],
Diazinon (Dimpylate) [O,O-diethyl-O-2-isopropyl-6-methylpyrimidin-4-ylphosphorothioate],
Chlorpyriphos [O,O-dimethyl-O-3,5,6-trichloro-2-pyridylphosphorothioate],
Acephate [O,S-dimethylacetylphosphoramidothioate],
Methidachion (DMTP) [S-2,3-dihydro-5-methoxy-2-oxo-1,3,4-thiadiazol-3-ylmethyl O,O-dimethylphosphorothiolothionate],
Disulfoton [O,O-diethyl S-2-ethylthioethyl phosphorothiolothionate],
Dichlorvos (DDVP) [2,2-dichlorovinyl dimethylphosphate],
Sulprofos [O-ethyl O-4-methylthiophenyl S-propyl phosphorodithioate],
Cyanophos [O-4-cyanophenyl-O,O-dimethylphosphorothioate],
Dioxabenzofos [2-methoxy-4H-1,3,2-benzodioxaphosphorin 2-sulfide],
Dimethoate [O,O-dimethyl-S-(N-methylcarbamoylmethyl) phosphorodithioate],
Phenthoate [S-ethoxycarbonylbenzyldimethyl phosphorothiolothionate],
Malathion [1,2-bis(ethoxylcarbonyl)-ethyl O,O-dimethyl phosphorothiolothionate],
Trichlorfon (Metrifonate) [dimethyl 2,2,2-trichloro-1-hydroxyethyl phosphonate],
Azinphos-methyl [S-(3,4-dihydro-4-oxo-1,2,3-benzotriazine-3-ylmethyl)dimethyl phosphorothiolothionate],
Monocrotophos [cis-3-(dimethoxyphosphinyloxy)-N-methylcrotonamide]and
Ethion [O,O,O',O'-tetraethyl S,S'-methylene bis (phosphorodithioate)].

Other examples are carbamate compounds such as
BPMC [O-sec butyl(phenylmethylcarbamate],
Benfuracarb [ethyl N-(2,3-dihydro-2,2-dimethylbenzofuran-7-yloxycarbonyl(methyl)aminothio)-N-isopropyl-β-allaninate],
Propoxur (PHC) [2-isopropoxy phenyl-N-methyl carbamate],
Carbosulfan [2,3-dihydro-2,2-dimethyl-7-benzo[b]furanyl N-dibutylaminothio-N-methyl carbamate],
Carbaryl [1-naphthyl-N-methylcarbamate],
Methomyl[S-methyl-N-((methylcarbamoyl)oxy) thioacetoimidate],
Ethiofencarb [2-(ethylthiomethyl)phenyl methylcarbamate],
Aldicarb [2-methyl-2-(methylthio)propanol O-( (methylamino)carbonyl)oxime],
Oxamyl [N,N-dimethyl-2-methylcarbamoyloxyimino-2-(methylthio)acetamide] and
Fenothiocarb [S-4-phenoxybutyl)-N,N-dimethylthiocarbamate].

Other examples include pyrethroid compounds such as
Ethofenprox [2-(4-ethoxyphenyl)-2-methylpropyl-3-phenoxybenzyl ether],
Fenvalerate [(RS)-α-cyano-3-phenoxybenzyl (RS)-2-(4-chlorophenyl)-3-methylbutyrate],
Esfenvalerate [(S)-α-cyano-3-phenoxybenzyl (S)-2-(4-chlorophenyl)-3-methylbutyrate],
Fenpropathrin [(RS)-α-cyano-3-phenoxybenzyl 2,2,3,3-tetramethylcyclopropanecarboxylate],
Cypermethrin [(RS)-α-cyano-3-phenoxybenzyl (1RS,3RS)-3-(2,2-dichlorovinyl)-2,2-dimethylcyclopropanecarboxylate],
Permethrin [3-phenoxybenzyl (1RS,3RS)-3-(2,2-dichlorovinyl)-2,2-dimethylcyclopropanecarboxylate],
Cyhalothrin [(RS)-α-cyano-3-phenoxybenzyl (Z)-(1RS)-cis-3-(2-chloro-3,3,3-trifluoropropen-1-yl)-2,2-dimethylcyclopropanecarboxylate],
Deltamethrin [(S)-α-cyano-3-phenoxybenzyl (1R,3R)-3(2,2-dibromovinyl)-2,2-dimethylcyclopropanecarboxylate],
Cycloprothrin [(RS)-α-cyano-3-phenoxybenzyl (RS)-2,2-dichloro-1-(4-ethoxyphenyl)cyclopropanecarboxylate],
Fluvalinate [α-cyano-3-phenoxybenzyl N-(2-chloro-α,α,α-trifluoro-p-tolyl)-D-valinate],
Bifenthrine [2-methylbiphenyl-2-ylmethyl) (Z)-(1RS)-cis-3-(2-chloro-3,3,3-trifluoropropen-1-yl)-2,2-dimethylcyclopropanecarboxylate],
Acrinathrin [(S)-(α)-cyano-(3-phenoxyphenyl)methyl (1R)-(1(S*),3α(Z))-2,2-dimethyl-3-(3-oxo-3-(2,2,2-trifluoro- 1-(trifluoromethyl)ethoxy-1-propenyl)
cyclopropanecarboxylate], 2-methyl-2-(4-bromodifluoromethoxyphenyl)propyl
(3-phenoxybenzyl)ether, Traromethrin[(S)-α-cyano-3-phenoxylbenzyl (1R,3R)-3-(
(1'RS)(1',1',2',2'-tetrabromoethyl))-2,2-
dimethylcyclopropanecarboxylate] and Silafluofen [4-ethoxylphenyl-(3-(4-fluoro-3-
phenoxyphenyl)propyl)dimethylsilane].

Other examples include thiadiazine derivatives such as

Buprofezin [2-t-butylimino-3-isopropyl-5-phenyl-1,3,5-
thiadiazin-4-one], nitroimidazolidine derivatives such as Imidachloprid [1-(6-chloro-3-pyridylmethl)-N-
nitroimidazolidine-2-indenamine], Cartap [S,S'-(2-dimethylaminotrimethylene)
bisthiocarbamate], Thiocyclam [N,N-dimethyl-1,2,3-trithian-5-ylamine], Bensultap [S,S'-2-dimethylaminotrimethylene
di(benzenethiosulfonate)], N-cyanoamidine derivatives such as N-cyano-N'-methyl-N'-
(6-chloro-3-pyridylmethyl)acetoamidine, chlorinated hydrocarbons such as Endosulfan
[6,7,8,9,10,10-hexachloro-1,5,5a,6,9,9a-hexahydro-6,9-
methanobenzo[e]-2,4,3-dioxathiepin 3-oxide], γ-BHC [1,2,3,4,5,6-hexachlorocyclohexane], 1,1-bis(chlorophenyl)-3,3,3-trichloroethanol, benzoylphenyl urea compounds such as Chlorofluazuron [1-(3,5-dichloro-4-(3-chloro-5-
trifluoromethylpyrid-2-yloxy)phenyl)-3-(2,6-
difluorobenzoyl)urea], Teflubenzuron [1-(3,5-dichloro-2,4-difluorophenyl)-3-(2,6-
difluorobenzoyl)urea] and Flufenoxron [1-(4-(2-chloro-4-trifluoromethylphenoxy)-2-
fluorophenyl)-3-(2,6-difluorobenzoyl)urea], formamidine derivatives such as Amitraz [N'-(2,4-dimethylphenyl)-N-((2,4-dimethylphenyl)
imino)methyl)-N-methylmethanimidamide] and Chlordimeform [N'-(4-chloro-2-methylphenyl)-N,N-
dimethylmethanimidamide], thio-urea derivatives such as Diaphenthiuron [N-(2,6-diisopropyl-4-phenoxyphenyl)-N'-
t-butylcarbodiimide], Bromopropylate [isopropyl 4,4'-dibromobenzilate], Tetradifon [2,4,5,4'-tetrachlorodiphenylsulfone], Quinomethionate [6-methyl-2-oxo-1,3-dithiolo-(4,6-b)-
quinoxaline], Propargite [2-(4-(1,1-dimethylethyl)phenoxy)-cyclohexyl
2-propynylsulfite], Fenbutatin oxide [bis(tris(2-methyl-2-phenylpropyl)tin)
oxide], Hexythiazox [(4RS,5RS)-5-(4-chlorophenyl)-N-
chlorohexyl-4-methyl-2-oxo-1,3-thiazolidine-3-
carboxamide], Chlofentezine [3,6-bis(2-chlorophenyl)-1,2,4,5-tetrazine], Pyridathioben[2-t-butyl-5-(4-t-butylbenzylthio)-4-
chloropyridazin-3(2H)-on], Phenpyroxymate [t-butyl(E)-4-((1,3-dimethyl-5-
phenoxypyrazol-4-yl)methyleneaminooxymethyl)
benzoate], Debphenpyrad [N-4-t-butylbenzyl-4-chloro-3-ethyl-1-
methyl-5-pyrazolcarboxamide], polynactin complexes including tetranactin, trinactin,
dinactin, Milbemectin, Avermectin, Ivermectin and
Azadilactin, and Pyrimidifen [5-chloro-N-(2-(4-(2-ethoxyethyl)-2,3-
dimethylphenoxy)ethyl)-6-ethylpyrimidine-4-amine].

When the present compound is applied as an active ingredient of insecticides, nematocides, and acaricides for agricultural use and active agents for controlling soil insect pests, the amount of application is generally 5 to 500 g per 1,000 m$^2$.

Emulsifiable concentrates, wettable powders and flowables such as water suspensions and emulsions are diluted with water to the concentration of 0.1 to 1000 ppm.

Granules and dusts are not diluted but used as prepared. When the present compound is applied as an active ingredient of insecticides and acaricides for house-hold use, emulsifiable concentrates, wettable powders and flowables are diluted with water to the concentration of 0.1 to 10000 ppm.

Oil solutions, aerosols, fumigants, volatile agents, fogging agents, ULV agents (formulations for ultra low volume applications), and poisonous baits are used as prepared.

The amount and concentration of application may be varied optionally according to the type of the formulations, time, place, and method of application, the type of noxious insect pests and the damage.

The invention will be further illustrated in detail by the production examples, formulation examples and biological tests although the invention is not limited in any sense to these examples.

EXAMPLE 1

540 mg of (1R)-trans-2,2-dimethyl-3-(2-methyl-1-propenyl)cyclopropanecarboxylic acid chloride was added under ice-water cooling to a mixed solution of 400 mg of (RS)-2-methyl-4-methylidene-3-ethylcyclopent-2-en-1-ol, 5 mg of 2,6-di-t-butyl-4-methylphenol and 274 mg of pyridine in 6 ml of toluene. The reaction was allowed to react at an ambient temperature for eight hours. The reaction solution was added to a 5% citric acid solution under ice-water cooling and extracted three times with diethyl ether. The combined ether layer was washed successively with a saturated sodium hydrogencarbonate solution and a saturated sodium chloride solution and dried over anhydrous magnesium sulfate. After removal of the solvent under reduced pressure, the obtained residue was subjected to silica gel column chromatography to yield 751 mg of (RS)-2-methyl-4-methylidene-3-ethyl-2-cyclopenten-1-yl (1R)-trans-2,2-dimethyl-3-(2-methyl-1-propenyl)cyclopropanecarboxylate (Compound No.1). Yield 72% (Eluent: n-hexane/ethyl acetate=30/1, 2,6-di-t-butyl-4-methylphenol 0.1%) $n_D^{20.5}$ 1.5070

$^1$H-NMR (CDCl$_3$, internal standard TMS) δ values (ppm): 1.05 (m, 3H), 1.11 (m, 3H), 1.27 (m, 3H), 1.41 (m, 1H), 1.70 (s, 6H), 1.79 (s, 3H), 2.05 (m, 1H), 2.15–2.49 (m, 3H), 2.90–3.10 (m, 1H), 4.75 (m, 1H), 4.70–4.96 (m, 2H), 5.50–5.71 (m, 1H).

IR (neat) $v_{max}$ (cm$^{-1}$): 1194, 1232, 1636, 1724, 2880, 2940, 2976

EXAMPLE 2

625 mg of (1R)-trans-3-(2,2-dichlorovinyl)-2,2-dimethylcyclopropanecarboxylic acid chloride was added under ice-water cooling to a mixed solution of 400 mg of (RS)-2-methyl-4-methylidene-3-ethylcyclopent-2-en-1-ol, 5 mg of 2,6-di-t-butyl-4-methylphenol and 274 mg of pyridine in 6 ml of toluene. The reaction was continued at an ambient temperature for eight hours. The reaction solution was added to a 5% citric acid solution under ice-water cooling, and extracted three times with diethyl ether. The combined ether layer was washed successively with a saturated sodium hydrogencarbonate solution and a saturated sodium chloride solution, and dried over anhydrous magnesium sulfate. After removal of the solvent under reduced pressure, the residue was subjected to silica gel column chromatography to yield 781 mg of (RS)-2-methyl-4-methylidene-3-ethyl-2-cyclopenten-1-yl (1R)-trans-3-(2,2-dichlorovinyl)-2,2-dimethylcyclopropanecarboxylate (Compound No.5). Yield 82%. (Eluent: n-hexane/ethyl acetate=30/1, 2,6-di-t-butyl-4-methylphenol 0.1%) $n_D^{23}$1.5251

$^1$H-NMR (CDCl$_3$, internal standard TMS) δ values (ppm): 1.04 (t, 3H), 1.19 (m, 3H), 1.29 (m, 4H), 1.62 (m, 1H), 1.80 (d, 3H), 2.11–2.52 (m, 3H), 2.88–3.10 (m, 1H), 4.78 (m, 1H), 4.87 (m, 1H), 5.53–5.75 (m, 2H)

EXAMPLE 3

Under ice-water cooling, 0.26 g of (1R)-cis,trans-2,2-dimethyl-3-(2-methyl-1-propenyl)-cyclopropanecarboxylic acid chloride was added dropwise to the solution of 0.21 g of (RS)-3-(1-methyl-2-propenyl)-4-methylidenecyclopent-2-en-1-ol and 0.14 ml of pyridine in 5 ml of toluene and then stirred at an ambient temperature for six hours. The reaction solution was poured into ice-water and extracted with ethyl acetate. The ethyl acetate layer was washed successively with 5% aqueous hydrochloric acid, water and a saturated sodium chloride solution, and dried over anhydrous magnesium sulfate. After removal of the solvent under reduced pressure, the obtained oily substance was subjected to silica gel column chromatography to yield 0.26 g of (RS)-3-(1-methyl-2-propenyl)-4-methylidenecyclopenten-2-yl (1R)-cis,trans-2,2-dimethyl-3-(2-methyl-1-propenyl)cyclopropanecarboxylate (Compound No.2). Yield 61% $n_D^{23}$1.5076

$^1$H-NMR (CDCl$_3$, internal standard TMS) δ values (ppm): 1.12–2.04 (m, 17H), 2.51 (m, 1H), 3.04 (m, 1H), 3.16 (m, 1H), 4.87–5.11 (m, 5H), 5.36–5.95 (m, 3H).

IR (neat) $v_{max}$ (cm$^{-1}$): 3092, 2976, 2936, 2880, 1726, 1642, 1614, 1452, 1424, 1380, 1318, 854

EXAMPLE 4

After 0.21 g of (RS)-3-(1-methyl-2-propenyl)-4-methylidenecyclopent-2-en-1-ol was dissolved in 5 ml of toluene, 0.14 ml of pyridine was added to the toluene solution. Under ice-water cooling, 70%(w/w) toluene solution containing 0.32 g of 2,2,3,3-tetramethylcyclopropanecarboxylic acid chloride was added dropwise to the mixed solution, and then stirred at an ambient temperature for six hours. The reaction solution was poured into ice-water and extracted with ethyl acetate. The ethyl acetate layer was washed successively with 5% aqueous hydrochloric acid and water, and vigorously stirred with 5% ammonia water for two hours. The ethyl acetate layer was then washed with a saturated sodium chloride solution and dried over anhydrous magnesium sulfate. After removal of the solvent under reduced pressure, the obtained oily substance was subjected to silica gel column chromatography to yield 0.24 g of (RS)-3-(1-methyl-2-propenyl)-4-methylidenecyclopenten-2-yl 2,2,3,3-tetramethylcyclopropanecarboxylate (Compound No.12). Yield 62% $n_D^{23}$1.5023

$^1$H-NMR (CDCl$_3$, internal standard TMS) δ values (ppm): 1.16–1.27 (m, 13H), 1.79 (s, 3H), 2.38 (m, 1H), 3.01 (m, 3H), 4.76 (s, 1H), 4.85 (s, 1H), 5.03 (m, 2H), 5.60 (brd, 1H), 5.78 (m, 1H).

IR (neat) $v_{max}$ (cm$^{-1}$): 3092, 2952, 1726, 1642, 1614, 1454, 1414, 1396, 1382, 1326, 844

EXAMPLE 5

After 0.26 g of (RS)-3-isopropyl-4-methylidenecyclopent-2-en-1-ol was dissolved in 5 ml of toluene, 0.23 ml of pyridine was added to the toluene solution. Under ice-water cooling, 0.55 g of (1RS)-cis-3-(Z-2-chloro-3,3,3-trifluoro-1-propenyl)-2,2-dimethylcyclopropanecarboxylic acid chloride was added dropwise to the mixed solution, and then stirred at an ambient temperature for six hours. The reaction solution was poured into ice-water and extracted with ethyl acetate. The ethyl acetate layer was washed successively with 5% aqueous hydrochloric acid, water, and a saturated sodium chloride solution, and dried over anhydrous magnesium sulfate. After removal of the solvent under reduced pressure, the obtained oily substance was subjected to silica gel column chromatography to yield 0.25 g of (RS)-3-isopropyl-4-methylidenecyclopenten-2-yl (1RS)-cis-3-(Z-2-chloro-3,3,3-trifluoro-1-propenyl)-2,2-dimethylcyclopropanecarboxylate (Compound No.6). Yield 39% $n_D^{26}$1.4804

$^1$H-NMR (CDCl$_3$, internal standard TMS) δ values (ppm): 1.14 (m, 6H), 1.24–1.32 (m, 6H), 1.95 (d, 1H), 2.12 (m, 1H), 2.44–2.66 (m, 2H), 2.96–3.09 (m, 1H), 4.93 (s, 1H), 5.01 (s, 1H), 5.64 (m, 1H), 5.86 (s, 1H), 6.93 (m, 1H)

IR (neat) $v_{max}$ (cm$^{-1}$): 3092, 2972, 2884, 1726, 1652, 1616, 1464, 1416, 1382, 1338, 868

EXAMPLE 6

Under ice-water cooling, 350 mg of (1R)-trans-3-(2-methyl-1-propenyl)-2,2-dimethylcyclopropanecarboxylic acid chloride was added dropwise to the mixed solution of 300 mg of (RS)-2-methyl-4-methylidene-3-(2,2,2-trifluoroethyl)cyclopent-2-en-1-ol, 5 mg of 2,6-di-tert-butyl-4-methylphenol, 185 mg of pyridine and 5 mg of 4-dimethylaminopyridine in 10 ml of dry terahydrofuran and then the resultant reaction mixture was allowed to react further 6 hours at room temperature. Then 10 ml of 10% aqueous ammonia solution was added to the solution and vigorously stirred for 2 hours. The reaction mixture was extracted three times with diethyl ether and the ether layers were combined. The combined layer was washed with brine and dried over anhydrous magnesium sulfate. After removal of the drying agent, the solvent was evaporated. The obtained residue was subjected to silica gel column chromatography to afford 280 mg of the desired (RS)-2-methyl-4-methylidene-3-(2,2,2-trifluoroethyl)cyclopent-2-en-1-yl (1R)-trans-3-(2-methyl-1-propenyl)-2,2-dimethylcyclopropanecarboxylate (Compound No.15). Yield 52% (Eluent: n-hexane/ethyl acetate=30/1, 2,6-di-tert-butyl-4-methylphenol 0.1% ) $n_D^{21}$1.4805

$^1$H-NMR (CDCl$_3$, internal standard TMS) δ values (ppm): 1.14 (m, 3H), 1.28 (m, 3H), 1.40 (m, 1H), 1.71 (m, 6H), 1.85 (d, 3H), 2.08 (m, 1H), 2.43 (m, 1H), 3.07 (m, 3H), 4.88 (m, 3H), 5.63 (brd, 0.5H), 5.70 (brd, 0.5H)

$^{19}$F-NMR (CDCl$_3$, internal standard CCl$_3$F) δ values (ppm): −64.35 (t, 3F).

EXAMPLE 7

430 mg of (1R)-trans-2,2-domethyl-3-(2,2-dichlorovinyl)cyclopropanecarboxylic acid chloride was used instead of (1R)-trans-3-(2-methyl-1-propenyl)-2,2-dimethylcyclopropanecarboxylic acid chloride in Example 6 above and the reaction procedures were carried out in a similar manner as in the example 6 to afford 410 mg of (RS)-2-methyl-4-methylidene-3-(2,2,2-trifluoroethyl)

cyclopent-2-en-1-yl (1R)-trans-2,2-dimethyl-3-(2,2-dichlorovinyl)cyclopropanecarboxylate (Compound No. 54). Yield 69% $n_D^{21}$ 1.4999

$^1$H-NMR (CDCl$_3$, internal standard TMS) δ values (ppm): 1.19 (m, 3H), 1.30 (m, 3H), 1.62 (m, 1H), 1.75 (d, 3H), 2.23 (m, 1H), 2.46 (m, 1H), 3.07 (m, 3H), 4.91 (d, 2H), 5.63 (m, 1.5H), 5.72 (brd, 0.5H).

$^{19}$F-NMR (CDCl$_3$ internal standard CCl$_3$F) δ values (ppm): −64.33(t, 3F).

EXAMPLE 8

A 70% toluene solution containing 430 mg of 2,2,3,3-tetramethylcyclopropanecarboxylic acid chloride was used instead of (1R)-trans-3-(2-methyl-1-propenyl)-2,2-dimethylcyclopropanecarboxylic acid chloride in Example 6 above and the reaction procedures were carried out in a similar manner as in Example 6 to afford 345 mg of (RS)-2-methyl-4-methylidene-3-(2,2,2-trifluoroethyl)cyclopent-2-en-1-yl 2,2,3,3-tetramethylcyclopropanecarboxylate (Compound No. 43). Yield 70% $n_D^{24}$ 1.4687

$^1$H-NMR (CDCl$_3$, internal standard TMS) δ values (ppm): 1.25 (m, 13H), 1.85 (s, 3H), 2.43 (m, 1H), 3.07 (m, 3H), 4.88 (d, 2H), 5.65 (brd, 1H).

$^{19}$F-NMR (CDCl$_3$, internal standard CCl$_3$F) δ values (ppm): −64.31(t, 3F).

EXAMPLE 9

370.25 mg of (2S)-2-(4-fluorophenyl)-3-methylbutyryl chloride was used instead of (1R)-trans-3-(2-methyl-1-propenyl)-2,2-dimethylcyclopropanecarboxylic acid chloride in Example 6 above and the reaction procedures were carried out in a similar manner as in Example 6 to afford 430 mg of (RS)-2-methyl-4-methylidene-3-(2,2,2-trifluoroethyl)cyclopent-2-en-1-yl (2S)-2-(4-fluorophenyl)-3-methylbutyrate (Compound No. 72). Yield 78% $n_D^{23}$ 1.4879

$^1$H-NMR (CDCl$_3$, internal standard TMS) δ values (ppm): 0.71 (m, 3H), 1.08 (d, 3H), 1.71 (d, 2H), 2.34 (m, 2H), 3.01 (m, 3H), 3.12 (d, 1H), 4.88 (m, 2H), 5.68 (m, 1H), 7.00 (m, 2H), 7.30 (m, 2H).

$^{19}$F-NMR (CDCl$_3$, internal standard CCl$_3$F) δ values (ppm): −116.01 (s, 1F), −64.32 (t, 3F).

EXAMPLE 10

After 0.20 g of (RS)-3-isopropyl-4-methylidenecyclopent-2-en-1-ol was dissolved in 5 ml of toluene, 0.15 ml of pyridine was added to the toluene solution. Under ice-water cooling, 0.31 g of (1R)-trans-3-(2-chloro-2-fluoroethenyl)-2,2-dimethylcyclopropanecarboxylic acid chloride was added dropwise to the mixed solution, and then stirred at an ambient temperature for six hours. The reaction solution was poured into ice-water and extracted with ethyl acetate.

The ethyl acetate layer was washed successively with 5% aqueous hydrochloric acid and water, then vigorously stirred with 5% ammonia water for two hours. The ethyl acetate layer was then washed with a saturated sodium chloride solution and dried over anhydrous magnesium sulfate. After removal of the solvent under reduced pressure, the obtained oily substance was subjected to silica gel column chromatography to yield 0.27 g of (RS)-3-isopropyl-4-methylidenecyclopenten-2-yl (1R)-trans-3-(2-chloro-2-fluoroethenyl)-2,2-dimethylcyclopropanecarboxylate (Compound No.17). Yield 60% $n_D^{23.5}$ 1.5014

$^1$H-NMR (CDCl$_3$ internal standard TMS) δ values (ppm): 1.11–1.28 (m, 12H), 1.50 (m, 1H), 1.97–2.23 (m, 1H), 2.43–2.66 (m, 2H), 2.97–3.10 (m, 1H), 4.63 (dd, 0.5H), 5.08 (dd, 0.5H), 4.92 (s, 1H), 5.00 (s, 1H), 5.66 (m, 1H), 5.88 (m, 1H).

IR (neat) $v_{max}$ (cm$^{-1}$): 3092, 2972, 2880, 1726, 1676, 1640, 1616, 1462, 1430, 1382, 1360, 1336, 850

EXAMPLE 11

823 mg of 1-ethyl-3-(3-dimethylaminopropyl)carbodiimide hydrochloride (WSC) was added to a solution of 500 mg of (RS)-2-methyl-4-methylidene-3-(2,2,2-trifluoroethyl)cyclopent-2-ene-1-ol, 500 mg of (1R)-trans-2,2-dimethyl-3-((E)-2-methoxycarbonyl-1-propenyl)cyclopropanecarboxylic acid and 580 mg of triethylamine in 10 ml of dichloromethane under ice-water cooling. The resulting reaction mixture was further allowed to react for 8 hours at room temperature. Then the reaction solution was poured into an ice-cooled 5% aqueous citric acid solution, and extracted three times with diethyl ether. The combined ether layer was washed with saturated sodium hydrogen carbonate and saturated sodium chloride solution, after dried over anhydrous magnesium sulfate, the solvent was evaporated under reduced pressure. The obtained residue was subjected to silica gel column chromatography to afford 823 mg of (RS)-2-methyl-4-methylidene-3-(2,2,2-trifluoroethyl)-2-cyclopent-1-yl (1R)-trans-2,2-dimethyl-3-((E)-2-methoxycarbonyl-1-propenyl)-cyclopropanecarboxylate (Compound No. 70). $n_D^{22}$ 1.4940

$^1$H-NMR (CDCl$_3$, internal standard TMS) δ values (ppm): 1.25 (d, 3H), 1.32 (d, 3H), 1.73 (m, 1H), 1.87 (d, 3H), 1.93 (s, 3H), 2.22 (m, 1H), 2.45 (m, 1H), 3.06 (m, 3H), 3.72 (s, 3H), 4.91 (d, 2H), 5.64 (brd, 0.5H), 5.76 (brd, 0.5H), 6.48 (d, 1H)

$^{19}$F-NMR (CDCl$_3$, internal standard CCl$_3$F) δ value (ppm): −64.35 (t, 3F)

EXAMPLE 12

A mixture of 12.5 ml of ether, 1.0 ml of t-butanol and 3.85 g of triphenylmethylphosphonium bromide was stirred at an ambient temperature, then 1.21 g of potassium t-butoxide was added to the mixture and stirred at an ambient temperature for five hours. Under ice-water cooling, 1.64 g of (RS)-3-(1-methyl-2-propenyl)4-oxocyclopent-2-en-1-ol dissolved in 2.0 ml of ether was added dropwise to the mixed solution and stirred for two hours. The mixture was subsequently stirred at an ambient temperature for six hours. The reaction solution was poured into a saturated aqueous sodium dihydrogen phosphate solution and extracted with ether. The organic layer was washed with a saturated sodium chloride solution, and dried over anhydrous magnesium sulfate. After removal of the solvent under reduced pressure, the obtained oily substance was subjected to silica gel column chromatography to yield 0.20 g of (RS)-3-(1-methyl-2-propenyl)-4-methylidenecyclopent-2-en-1-ol. Yield 12%

$^1$H-NMR (CDCl$_3$, internal standard TMS) δ values (ppm): 1.24 (t, 3H), 1.56 (brs, 1H), 2.43 (m, 1H), 3.00 (m, 1H), 3.15 (m, 1H), 4.80–5.10 (m, 5H), 5.79–5.95 (m, 2H).

EXAMPLE 13

2.02 Grams of (RS)-3-(1-methyl-2-propenyl)-4-methylidenecyclopent-2-en-1-yl t-butyldimethylsilyl ether was dissolved in 20 ml of tetrahydrofuran. Under ice-water cooling, 7.7 ml of a tetrahydrofuran solution of 1M n-tetrabutylammonium fluoride was added to the ether solution, and then stirred at an ambient temperature for six hours. The reaction solution was poured into ice-water and extracted with ether. The ether layer was washed with a saturated sodium chloride solution, and dried with anhydrous magnesium sulfate. After removal of the solvent under reduced pressure, the oily substance obtained was subjected to silica gel column chromatography to yield 1.05 g of (RS)-3-(1-methyl-2-propenyl)-4-methylidenecyclopent-2-en-1-ol. Yield 91%

$^1$H-NMR (CDCl$_3$, internal standard TMS) δ values (ppm): 1.24 (t, 3H), 1.56 (brs, 1H), 2.42 (m, 1H), 2.99 (m, 1H), 3.15 (m, 1H), 4.81–5.10 (m, 5H), 5.80–5.95 (m, 2H)

EXAMPLE 14

Under stirring, 9.65 g of potassium t-butoxide was added over 10 minutes to a mixed solution of 7 g of t-butanol and 30.7 g of triphenylmethylphosphonium bromide in 85 ml of diethyl ether. The mixed solution was allowed to react at an ambient temperature for eight hours, and then cooled to 0° C. A solution prepared by dissolving 9 g of (RS)-4-hydroxy-3-methyl-2-ethylcyclopent-2-en-1-one in 10 ml of diethyl ether was added to the mixed solution over 10 minutes. After the reaction solution was warmed over two hours from 0° C. to the room temperature, the solution was further allowed to react for eight hours. The reaction solution was then added to 100 ml of a saturated aqueous sodium dihydrogen phosphate solution, and extracted three times with 100 ml of diethyl ether. The combined organic layer was dried over anhydrous magnesium sulfate. After removal of the solvent under reduced pressure, the residue was dissolved in ether, stirred for two minutes, and filtered through Celite (registered trade mark by Johns-Manville). The filtrate was concentrated under reduced pressure, and the residue obtained was treated by silica gel column chromatography to yield 5.8 g of (RS)-2-methyl-4-methylidene-3-ethylcyclopent-2-en-1-one. Yield 65% (Eluent: n-hexane/ethyl acetate=5/1 (v/v))

$^1$H-NMR (CDCl$_3$ internal standard TMS) δ values (ppm): 1.02 (t, 3H), 1.42 (m, 1H), 1.82 (s, 3H), 2.20 (q, 2H), 2.31 (m, 0.5H), 2.38 (m, 0.5H), 2.87–3.01 (m, 1H), 4.58 (m, 1H), 4.72 (m, 1H), 4.81 (m, 1H)

EXAMPLE 15

After 4.0 g of (RS)-2-methyl-4-methylidene-3-ethyl-1-t-butyldimethylsilyloxy-2-cyclopentene was dissolved in 35 ml of dry tetrahydrofuran, 17.5 ml of a 1M tetrabutylammonium fluoride/tetrahydrofuran solution was added under cooling and stirred at ambient temperatures for twelve hours. The reaction solution was then added to 100 ml of an ice-cooled 5% aqueous oxalic acid, and extracted with diethyl ether (300 ml×3 times). The combined ether layer was washed successively with a saturated sodium hydrogencarbonate solution and a saturated sodium chloride solution, and dried over anhydrous magnesium sulfate. After removal of the solvent under reduced pressure, the residue was treated by silica gel column chromatography (eluent: n-hexane:ethyl acetate=3:1 (v/v)) to yield 2.0 g of (RS)-2-methyl-4-methylidene-3-ethylcyclopent-2-en-1-ol. Yield 92%

$^1$H-NMR (CDCl$_3$, internal standard TMS) δ values (ppm): 1.02 (t, 3H), 1.42 (m, 1H), 1.82 (s, 3H), 2.02 (q, 2H), 2.31 (m, 0.5H), 2.38 (m, 0.5H), 2.87–3.01 (m, 1H), 4.58 (m, 1H), 4.72 (m, 1H), 4.81 (m, 1H).

EXAMPLE 16

After 10.5 g of (RS)-2-methyl-4-methylidene-3-(2,2,2-trifluoroethyl)-1-t-butyldimethylsilyloxy-2-cyclopentene was dissolved in 50 ml of dry tetrahydrofuran, a mixture of 10.5 ml of a 1M tetrabutylammonium fluoride/tetrahydrofuran solution and 5 ml of hydrofluoric acid was added under cooling and stirred at ambient temperatures for twelve hours. The reaction solution was then added to 100 ml of an ice-cooled 5% aqueous oxalic acid, and extracted with diethyl ether (300 ml×3 times). The combined ether layer was washed successively with a saturated sodium hydrogencarbonate solution and a saturated sodium chloride solution, and dried over anhydrous magnesium sulfate. After removal of the solvent under reduced pressure, the residue was treated by silica gel column chromatography (eluent: n-hexane:ethyl acetate=3:1 (v/v)) to yield 5.27 g of (RS)-2-methyl-4-methylidene-3-(2,2,2-trifluoroethyl)cyclopent-2-en-1-ol. Yield 80%

$^1$H-NMR (CDCl$_3$, internal standard TMS) δ values (ppm): 1.91 (s, 3H), 2.43 (m, 1H), 3.02 (m, 3H), 4.18 (brs, 1H), 4.85 (d, 2H).

$^{19}$F-NMR (CDCl$_3$, internal standard CCl$_3$F) δ value (ppm): −64.37 (t, 3F)

EXAMPLE 17

A suspension prepared by suspending 3.7 g of zinc dust in 30 ml of tetrahydrofuran was mixed with 1.4 ml of dibromomethane in an atmosphere of argon at a temperature of −20° to −10° C. After stirring for fifteen minutes, 12.5 ml of a dichloromethane solution of 1M titanium tetrachloride was added dropwise to the suspension and stirred at the above temperatures for thirty minutes and at 4° C. for three days. A solution prepared by dissolving 3.33 g of (RS)-3-(1-methyl-2-propenyl)-4-oxocyclopent-2-en-1-yl t-butyldimethylsilyl ether in 15 ml of dichloromethane was added dropwise to the reaction solution in an atmosphere of argon at a temperature of −20° to −10° C. After stirring at an ambient temperature for six hours, 30 ml of hexane was further added to the reaction solution. Under stirring, a suspension prepared by suspending 15 g of sodium hydrogencarbonate in 100 ml of water was added gradually to the reaction solution. After stirring at an ambient temperature for two hours, the reaction solution was filtered through celite, extracted with hexane, and dried over anhydrous magnesium sulfate. After removal of the solvent under reduced pressure, the obtained oily substance was subjected to silica gel column chromatography to yield 2.02 g of (RS)-3-(1-methyl-2-propenyl)-4-methylidenecyclopent-2-en-1-yl t-butyldimethylsilyl ether. Yield 61%

$^1$H-NMR (CDCl$_3$, internal standard TMS) δ values (ppm): 0.08 (d, 6H), 0.90 (s, 9H), 1.23 (dd, 3H), 2.42 (m, 1H), 2.92 (m, 1H), 3.12 (m, 1H), 4.81–5.11 (m, 5H), 5.79–5.97 (m, 2H).

EXAMPLE 18

13.04 Grams of dibromomethane and 14.71 g of zinc dust were mixed in 120 ml of dried tetrahydrofuran and cooled to 0° to 5° C. After 50 ml of a dichloromethane solution of 1M titanium tetrachloride was added dropwise to the mixed solution over fifteen minutes, the reaction was continued at a temperature of 0° to 5° C. for three days.

A solution prepared by 12.67 g of (RS)-4-t-butyldimethylsilyloxy-3-methyl-2-ethylcyclopent-2-en-1-one in 50 ml of dichloromethane was added dropwise to the reaction solution at the temperatures of 0° to 5° C. over fifteen minutes. After the reaction was run at the same temperatures for one hour, a mixture of 10 mg of 2,6-di-t-butyl-4-methylphenol and 100 ml of hexane and slurry containing 105 g of sodium hydrogencarbonate and 70 ml of water were successively added to the reaction solution.

After stirring at a temperature of 0° to 5° C. for two hours, the organic layer was decanted and the residue was extracted three times with 150 ml of n-hexane. The combined organic layer was washed with a saturated sodium hydrogencarbonate solution, and dried over anhydrous magnesium sulfate. After removal of the solvent under reduced pressure, the residue was subjected to silica gel column chromatography to yield 7.71 g of (RS)-2-methyl-4-methylidene-3-ethyl-1-t-butyldimethylsilyloxy-2-cyclopentene. Yield 62% (Eluent: n-hexane/ethyl acetate=20/1 (v/v))

$^1$H-NMR (CDCl$_3$, internal standard TMS) δ values (ppm): 0.1 (m, 6H), 0.89 (s, 9H), 1.00 (s, 3H), 1.75 (s, 3H), 2.19 (q, 2H), 2.25–2.40 (m, 1H), 2.78–2.91 (m, 1H), 4.64 (m, 2H), 4.73 (m, 1H).

EXAMPLE 19

10.01 Grams of dibromomethane and 11.51 g of zinc dust were mixed in 100 ml of dried tetrahydrofuran and cooled to −40° C. After 4.52 ml of titanium tetrachloride was added dropwise to the mixed solution over two minutes, the reaction was continued at a temperature of 0° to 5° C. for three days.

A solution prepared by 12.34 g of (RS)-4-t-butyldimethylsilyloxy-3-methyl-2-(2,2,2-trifluoroethyl)cyclopent-2-en-1-one in 20 ml of dichloromethane was added dropwise to the reaction solution at the temperature. After the reaction was run at the same temperatures for one hour, a mixture of 10 mg of 2,6-di-t-butyl-4-methylphenol and 100 ml of hexane and slurry containing 105 g of sodium hydrogencarbonate and 70 ml of water were successively added to the reaction solution.

After stirring at a temperature of 0° to 5° C. for two hours, the organic layer was decanted and the residue was extracted three times with 150 ml of n-hexane. The combined organic layer was washed with a saturated sodium hydrogencarbonate solution, and dried over anhydrous magnesium sulfate. After removal of the solvent under reduced pressure, the residue was subjected to silica gel column chromatography to yield 10.5 g of (RS)-2-methyl-4-methylidene-3-(2,2,2-trifluoroethyl)-1-t-butyldimethylsilyloxy-2-cyclopentene. Yield 85.7% (Eluent: n-hexane/ethyl acetate=20/1 (v/v))

$^1$H-NMR (CDCl$_3$, internal standard TMS) δ values (ppm): 0.08 (d, 6H), 0.92 (s, 9H), 1.83 (s, 3H), 2.42 (m, 1H), 2.91 (m, 1H), 3.01 (q, 2H), 4.71 (brs, 1H), 4.78 (d, 2H).

$^{19}$F-NMR (CDCl$_3$, internal standard CCl$_3$F) δ value (ppm): −64.42 (t, 3F)

EXAMPLE 20

1.43 Grams of imidazole was added to a solution prepared by dissolving 2.71 g of (RS)-3-(1-methyl-2-propenyl)-4-oxo-2-cyclopent-2-en-1-ol in 30 ml of N,N-dimethylformamide. Under ice-water cooling, 2.95 g of t-butyldimethylsilyl chloride was added to the mixed solution with stirring. After stirring at ambient temperatures for six hours, the reaction solution was poured into icy cold water and extracted with ether. The ether layer was washed successively with 10% aqueous citric acid and a saturated sodium chloride solution, and dried over anhydrous magnesium sulfate. After removal of the solvent under reduced pressure, the obtained oily substance was subjected to silica gel column chromatography to yield 3.33 g of (RS)-3-(1-methyl-2-propenyl)-4-oxocyclopent-2-en-1-yl t-butyldimethylsilyl ether. Yield 70%

$^1$H-NMR (CDCl$_3$, internal standard TMS) δ values (ppm): 0.10–0.12 (m, 6H), 0.91 (s, 9H), 1.20 (t, 3H), 2.28 (dd, 1H), 2.75 (dd, 1H), 3.24 (m, 1H), 4.88 (m, 1H), 5.00–5.10 (m, 2H), 5.86 (m, 1H), 7.01 (m, 1H).

EXAMPLE 21

After 10 g of (RS)-4-hydroxy-3-methyl-2-ethylcyclopent-2-en-1-one and 5.78 g of imidazole were dissolved in 100 ml of dry dimethylformamide, 11.91 g of t-butyldimethylchlorosilane was added to the solution at an ambient temperature. After stirring at an ambient temperature for 14 hours, the reaction solution was added to 5% aqueous citric acid under ice-water cooling, and extracted three times with diethyl ether. The combined organic layer was washed successively with a saturated sodium hydrogencarbonate solution and a saturated sodium chloride solution, and dried with anhydrous magnesium sulfate. After removal of the solvent under reduced pressure, the residue was subjected to silica gel column chromatography to yield 14.231 g of (RS)-4-t-butyldimethylsilyloxy-3-methyl-2-ethylcyclopent-2-en-1-one. Yield 82% (Eluent: n-hexane/ethyl acetate=5/1 (v/v))

$^1$H-NMR (CDCl$_3$, internal standard TMS) δ values (ppm): 0.11 (m, 6H), 0.91 (s, 9H), 1.00 (t, 3H), 2.01 (s, 3H), 2.12–2.31 (m, 3H), 2.69 (dd, 1H), 4.65 (m, 1H).

EXAMPLE 22

After 10 g of (RS)-4-hydroxy-3-methyl-2-(2,2,2-trifluoroethyl)cyclopent-2-en-1-one and 4.2 g of imidazole were dissolved in 100 ml of dry dimethylformamide, 8.54 g of t-butyldimethylchlorosilane was added to the solution at an ambient temperature. After stirring at an ambient temperature for 12 hours, the reaction solution was added to 5% aqueous citric acid under ice-water cooling, and extracted three times with diethyl ether. The combined organic layer was washed successively with a saturated sodium hydrogencarbonate solution and a saturated sodium chloride solution, and dried with anhydrous magnesium sulfate. After removal of the solvent under reduced pressure, the residue was subjected to silica gel column chromatography to yield 14.3 g of (RS)-4-t-butyldimethylsilyloxy-3-methyl-2-(2,2,2-trifluoroethyl)cyclopent-2-en-1-one. Yield 90% (Eluent: n-hexane/ethyl acetate=5/1 (v/v))

$^1$H-NMR (CDCl$_3$, internal standard TMS) δ values (ppm): 0.14 (d, 6H), 0.92 (s, 9H), 2.12 (s, 3H), 2.30 (dd, 1H), 2.81 (dd, 1H), 3.08 (m, 2H), 4.78 (brd, 1H).

$^{19}$F-NMR (CDCl$_3$, internal standard CCl$_3$F) δ value (ppm): −65.07 (t, 3F)

Preparation of (RS)-4-hydroxy-3-methyl-2-ethylcyclopent-2-en-1-one

1. Under an atmosphere of nitrogen, 10 ml of tetrahydrofuran and 10 mg of iodine were mixed with 3.974 g of magnesium flakes. With stirring, 3 ml of a solution prepared by dissolving 22.28 g of ethyl bromide in 25 ml of tetrahydrofuran was added dropwise to the mixture. The residual tetrahydrofuran solution of ethyl bromide was added dropwise to the reaction vessel placed in a water bath over one hour. After stirring for thirty minutes, a solution prepared by dissolving 15 g of 5-methyl-2-furaldehyde in 5 ml of tetrahydrofuran was added dropwise to the reaction solution over five minutes under ice-water cooling. After one hour, the reaction solution was added to a cooled 10% ammonium chloride solution and stirred for five minutes. The mixed solution was extracted twice with diethyl ether. The combined ether layer was washed twice with a saturated sodium chloride solution, and dried over anhydrous magnesium sulfate. After removal of the solvent under reduced pressure, the residue was distilled, and a distillate fraction of 95° to 98° C. at 22 mmHg was collected to yield 28.977 g of 1-(5-methyl-2-furyl)propanol. Yield 91% b.p.: 95°–98° C. (22 mmHg)

$^1$H-NMR (CDCl$_3$, solvent, internal standard TMS) δ values (ppm): 0.97 (t, 3H), 1.78–2.02 (m, 3H), 2.29 (s, 3H), 4.51 (m, 1H), 5.89 (d, 1H), 6.11 (d, 1H).

2. A mixed solution of 28.97 g of the 1-(5-methyl-2-furyl) propanol thus obtained, 0.394 g of 50% aqueous acetic acid, 0.394 g of a 23% (w/v) sodium hydroxide solution in 579.4 g of water was heated and refluxed at the constant pH of 5.70 to 5.85 for 38 hours. After the mixed solution was cooled to the room temperature, a 23% (w/v) sodium hydroxide solution was added to the mixed solution to adjust the pH of the solution to 8.0 to 8.2, and then refluxed for three hours. A 50% acetic acid solution was added to the refluxing solution to adjust the pH to 6.0 to 6.5. The reaction solution was then cooled to the room temperature, mixed with 300 g of sodium chloride, and extracted three times with 500 ml of diethyl ether. The combined ether layer was washed twice with a saturated sodium chloride solution and dried over anhydrous magnesium sulfate. After removal of the solvent under reduced pressure, the residue was distilled, and a distillate fraction of 157° to 162° C. at 19 mmHg was collected to yield 15 g of (RS)-4-hydroxy-3-methyl-2-ethylcyclopent-2-en-1-one. Yield 52% b.p.: 157°–162° C. (19 mmHg)

$^1$H-NMR (CDCl$_3$, internal standard TMS) δ values (ppm): 1.01 (t, 3H), 1.92 (m, 1H), 2.08 (s, 3H), 2.21 (q, 2H), 2.26 (dd, 1H), 2.78 (dd, 1H), 4.71 (m, 1H).

Preparation of (RS)-2-methyl-3-(2,2,2-trifluoroethyl)-4-oxocyclopent-2-en-1-ol

1. A mixed solution of 123 g of potassium hydroxide, 900 ml of methanol and 80 ml of water was added to 160 g of ethyl 4,4,4-trifluorobutylate with stirring under ice-water cooling and then the reaction mixture was allowed to react for 12 hours at room temperature. The resultant reaction solution was concentrated under reduced pressure to obtain a residue, which was then partitioned between water and diethyl ether. The separated ether layer was once washed with water and the separated aqueous layer was combined with the previously obtained aqueous layer. An ice-cooled 10% hydrochloric acid solution was added to the combined aqueous solution so that the pH of the solution was 1. Then the acidic solution was extracted three times with diethyl ether. The layers were combined and washed twice with brine, and dried over anhydrous magnesium sulfate. The filtered solution was evaporated under reduced pressure to yield 131 g of the desired 4,4,4-trifluorobutyric acid. Yield 98%

$^1$H-NMR (CDCl$_3$, internal standard TMS) δ values (ppm): 2.52 (m, 2H), 2.67 (t, 2H).

2. 101 ml of oxalyl chloride and 0.1 ml of dimethylformamide was added to a solution of thus obtained 131 g of the 4,4,4-trifluorobutyric acid in 1 liter of pentane, and the resultant solution was refluxed for three hours. Then the reaction solution was distilled to yield 112 g of 4,4,4-trifluorobutyryl chloride in a yield of 76%. (b.p. 103° C./760 mmHg)

3. 0.1 ml of carbon tetrachloride was added to a mixture of 20.35 g of magnesium(turnings) and 148 ml of ethanol and then heated at 55° C. A mixed solution of 197 ml of ethanol, 700 ml of diethyl ether and 168 g of diethyl malonate was added to the reaction mixture over 1 hour. Two hours later the reaction solution was cooled to −5° C. and 112 g of 4,4,4-trifluorobutyryl chloride was added to the solution under an atmosphere of nitrogen, then the resultant reaction mixture was left at an ambient temperature for 1 hour. Then the mixture was allowed to react further 12 hours. After completion of the reaction, the reaction solution was poured into a 5% hydrochloric acid solution and extracted three times with diethyl ether. The ether layers were combined and washed twice with brine and dried over anhydrous magnesium sulfate. The filtered ether solution was evaporated under reduced pressure. The obtained residue was distilled under reduced pressure to yield 179 g of the desired 4,4,4-trifluorobutyrylmalonic acid diethyl ester in a yield of 90%. (b.p. 125°–134° C., 15 mmHg)

$^1$H-NMR (CDCl$_3$, internal standard TMS) δ values (ppm): 1.32 (t, 3H), 2.50 (m, 2H), 2.95 (t, 2H), 4.29 (q, 2H), 4.50 (s, 1H).

4. A mixture of 179 g of the 4,4,4-trifluorobutyrylmalonic acid ditheyl ester thus obtained, 260 ml of water and 322 mg of p-toluenesulfonic acid was refluxed with vigorous stirring for 6 hours. The reaction solution was then poured into saturated aqueous sodium hydrogencarbonate solution and extracted three times with diethyl ether. The ether layers were combined and the combined layer was washed with brine, dried over anhydrous magnesium sulfate. After the drying agent was removed, the solvent was removed under reduced pressure. The obtained residue was distilled inder reduced pressure to yield 98.8 g of the desired ethyl 4,4,4-trifluorobutyrylacetate in a yield of 74%. (b.p. 93°–97° C., 15 mmHg)

$^1$H-NMR (CDCl$_3$, internal standard TMS) δ values (ppm): 1.28 (t, 3H), 2.45 (m, 2H), 2.96 (t, 2H), 3.48 (s, 1H), 4.22 (q, 2H).

5. 98.8 g of the ethyl 4,4,4-trifluorobutyrylacetate thus obtained was added to 250 ml of a 10% sodium hydroxide solution and vigorously stirred for 12 hours. The pH value of the reaction solution was brought 7.5 with a 10% aqueous sulfuric acid solution. Then 250 ml of toluene, 2.86 g of sodium hydrogencarbonate and 6.43 g of hydrosulfite were added to the solution under an atmosphere of nitrogen and warmed to 37° C. 90 g of methyl glyoxal was added over 1 hour and allowed to react for 12 hours. After 50 g of sodium chloride was added to the solution, the mixture was extracted three times with ethyl acetate. The ethyl acetate layers were combined and dried over anhydrous magnesium sulfate. After removal of the drying agent, the solvent was removed under reduced pressure. The obtained residue was mixed with 450 ml of 5% sodium hydroxide solution and vigorously stirred under ice-water cooling. The pH of the solution was adjusted to 7.3 with a 10% hydrochloric acid solution and then extracted three times with ethyl acetate. The ethyl acetate layer was combined and dried over anhydrous magnesium sulfate. After removal of the drying agent, the solvent was removed under reduced pressure. The obtained residue was distilled under reduced pressure to afford 45 g of the desired (RS)-2-methyl-3-(2,2,2-trifluoroethyl)-4-oxocyclopent-2-en-1-ol in a yield of 50%. (b.p. 100°–133° C., 0.52 mmHg)

$^1$H-NMR (CDCl$_3$, internal standard TMS) δ values (ppm): 2.19 (s, 3H), 2.35 (dd, 1H), 2.85 (dd, 1H), 3.08 (q, 2H), 4.82 (brd, 1H).

$^{19}$F-NMR (CDCl$_3$, internal standard CCl$_3$F) δ values (ppm): −65.1(t, 3F).

Formulation examples are described below, parts represent parts by weight.

Formulation example 1 Emulsifiable concentrates

Twenty parts of each of the compounds 1 to 90 are dissolved in 65 parts of xylene, mixed with 15 parts of an emulsifier Solpol 3005X (registered trade mark by Toho Chemical), and stirred sufficiently to give 20% emulsifiable concentrates for each compound.

Formulation example 2 Wettable powders

Forty parts of each of the compounds 1 to 90 are mixed first with 5 parts of Solpol 3005X and then with 32 parts of Carprex #80 (synthetic hydrated silicon hydroxide fine powder: registered trade mark by Shionogi & Co. Ltd.) and 23 parts of 300-mesh diatomaceous earth, and stirred with a blender to give 40% wettable powders for each compound.

Formulation example 3 Granules 1.5% granules for each of compounds 1 to 90 are obtained by sufficiently mixing 1.5 parts of each of the compounds and 98.5 parts of AGSORBLVM-MS 24/48 (granular carrier of calcined montmorillonite having the particle diameter of 24 to 48 meshes by OIL DRI Corp.) with each other.

Formulation example 4 Microcapsules

A mixture of 10 parts of each of the compounds 1 to 90, 10 parts of phenylxylylethane, and 0.5 part of 5 Sumijul L-75 (tolylene diisocyanate by Sumitomo Bayer Urethane Ltd.) is added to 20 parts of a 10% aqueous solution of gum arabic, and stirred with a homomixer to give an emulsion having the mean particle diameter of 20 μm. The emulsion is further mixed with two parts of ethylene glycol and allowed to react in a warm bath of 60° C. for 24 hours to give a microcapsule slurry.

A thickening agent is prepared by dispersing 0.2 parts of xanthan gum and 1.0 part of Veegum R (aluminum magnesium silicate by Sanyo Chemical) in 56.3 parts of ion-exchanged water.

10% microcapsules are obtained by mixing 42.5 parts of the microcapsule slurry and 57.5 parts of the thickening agent for each of the compounds.

Formulation example 5 Flowables (Water emulsion)

Each of the mixtures of 10 parts of each of the compounds 1 to 90 and 10 parts of phenylxylylethane is added to 20 parts of a 10% aqueous solution of polyethylene glycol, and stirred with a homomixer to give an emulsion having the mean particle diameter of 3 μm.

A thickening agent is obtained by dispersing 0.2 part of xanthan gum and 1.0 part of Veegum R (aluminum magnesium silicate by Sanyo Chemical) in 58.8 parts of ion-exchanged water. 10% water emulsion is obtained by mixing 40 parts of the emulsion and 60 parts of the thickening agent for each of the compounds.

Formulation example 6 Dusts

Five parts of each of the compounds 1 to 90 are mixed with 3 parts of Carprex #80, 0.3 part of PAP, and 91.7 part of 300-mesh talc and stirred with a blender to give 5% dusts for each of the compounds.

Formulation example 7 Oil solutions 0.1% oil solutions are obtained by dissolving 0.1 part of each of the compounds 1 to 90 in 5 parts of dichloromethane and mixing the solution with 94.9 parts of deodorized kerosine for each of the compounds.

Formulation example 8 Oil-based aerosols

One part of each of the compounds 1 to 90 is mixed dissolved in 5 parts of dichloromethane and 34 parts of deodorized kerosine. Oil-based aerosol is obtained for each of the compounds by filling an aerosol vessel with the mixture and charging 60 parts of a propellant (liquefied petroleum gas) through a valve into the aerosol vessel under pressure.

Formulation example 9 Water-based aerosols

An aerosol vessel is filled with 50 parts of pure water and a mixture of 0.6 parts of each of the compounds 1 to 90, 5 parts of xylene, 3.4 parts of deodorized kerosine, and 1 part of an emulsifier Atmos 300 (registered trade mark by Atlas Chemical). Water-based aerosol is obtained for each of the compounds by charging 40 parts of a propellant (liquefied petroleum gas) through a valve into the aerosol vessel under the applied pressure.

Formulation example 10 Mosquito-coils

A solution prepared by dissolving 0.3 g of each of the compounds 1 to 90 in each 20 ml of acetone is homogeneously mixed with 99.7 g of a carrier for a mosquito-coil (mixture of powder of *Machilus thunbergii* Sieb. et Zucc., lees powder and wood powder at the ratio of 4:3:3). After 120 ml of water is added, the mixture is kneaded sufficiently, molded, and dried to give mosquito-coil for each of the compounds.

Formulation example 11 Mosquito-mats for electric heating fumigation

A total 10 ml of a solution is prepared by dissolving 0.8 g of each of the compounds 1 to 90 and 0.4 g of piperonyl butoxide in acetone. Each mosquito-mat for electric heating fumigation is obtained by impregnating a base material (a plate of compacted fibrils of a mixture of pulp and cotton linters: 2.5 cm×1.5 cm×0.3 cm) homogeneously with 0.5 ml of the solution.

Formulation example 12 Solutions for electric heating fumigation

Heating fumigation comprising dipping a part of porous absorptive wick, which is prepared by calcinating a caking of a powdery inorganic substance with a binding agent, in a solution of 3 parts of each of the compounds 1 to 90 in 97 parts of deodorized kerosine contained in a vessel of vinyl chloride and indirectly heating the wick around the top to fumigate the compound.

Formulation example 13 Fumigants

Fumigant is prepared for each of the compounds 1 to 90 by impregnating a porous ceramic plate (4.0 cm×4.0 cm×1.2 cm) with a solution prepared by dissolving 100 mg of each of the compounds 1 to 90 in an appropriate amount of acetone.

Formulation example 14 Volatile agents

Volatile agent is prepared for each of the compounds 1 to 90 by applying a solution, prepared by dissolving 100 mg of each of the compounds in an appropriate amount of acetone, onto filter paper (2 cm×2 cm×0.3 mm) and evaporating the acetone.

Formulation example 15 Mite-repellent sheets

Mite-repellent sheet is prepared by impregnating filter paper with an acetone solution containing each of the compounds 1 to 90 so that the concentration of each of the compounds is 1 g/1 m$^2$ and evaporating the acetone.

The compounds of the present invention were respectively tested as an active ingredient of an insecticide, an acaricide, or a soil insect pest. In the description below, the compounds are shown by the numbers in Tables 1 whereas compounds used as controls ((RS)-isomer on the alcohol site and dl-cis, trans isomer on the acid site) are shown by the symbols in Table 2.

TABLE 2

| Symbols for chemical compound | Chemical Structure | Remarks |
|---|---|---|
| A | (structure) | A compound disclosed in Japanese Patent Kokai (Laying Open) S-56-75459 as a compound 1-A |
| B | (structure) | A compound disclosed in Japanese Patent Kokai (Laying Open) S-57-67537 as a compound (1) |
| C | (structure) | Allethrin commercial insecticide |

Biological test 1

Each compound was formulated into an emulsifiable concentrates according to Formulation example 1. Five milliliters of the emulsifiable concentrates previously diluted with water were mixed with 50 g of sterilized soil (16 mesh) so that the concentration of the active ingredient in soil was 10 ppm. The soil was placed in a polyethylene cup (diameter: 5.6 cm, depth: 5.8 cm), and two corn grains germinated to have the root of approximately 2 cm were planted in the soil. Ten 3-instar larvae of *Diabrotica undecimpunctata howardi* Barber were left on the soil. After three days, the mortality of the larvae and the damage of the grains were observed. The damage was evaluated according to the following criteria:

| Damage | Criteria |
|---|---|
| ++ | equivalent damage to non-treated soil |
| + | heavy damage |
| +− | slight damage |
| − | no damage |

Table 3 shows the mortality of the larvae (%) and evaluation of the damage.

TABLE 3

| Compound | Mortality (%) | Damage |
|---|---|---|
| 1 | 100 | — |
| 4 | 100 | — |
| 5 | 100 | — |
| 9 | 100 | — |
| 11 | 100 | — |
| 12 | 100 | — |
| 15 | 100 | — |
| 20 | 100 | — |

TABLE 3-continued

| Compound | Mortality (%) | Damage |
|---|---|---|
| 21 | 100 | — |
| 27 | 100 | — |
| 43 | 100 | — |
| 44 | 100 | — |
| 54 | 100 | — |

Biological test 2

The present compound was diluted with acetone, applied homogeneously onto a bottom of an aluminum plate (inner diameter: 10 cm; depth: 3 cm; bottom area: 78.5 cm$^2$) at the concentration of 100 mg/m$^2$, and air-dried. Ten cockroaches (*Blattella germanica*) including five males and five females were left on and forcibly brought into contact with the treated face of the aluminum plate. After two hours, the rate of knocked-down insects was examined, and the results are shown in Table 4.

TABLE 4

| Compound | Rate of knocked-down insects (%) |
|---|---|
| 1 | 100 |
| 5 | 100 |
| 6 | 100 |
| 8 | 100 |
| 9 | 100 |
| 10 | 100 |
| 11 | 100 |
| 12 | 100 |
| 14 | 100 |
| 17 | 100 |
| 19 | 100 |
| 20 | 100 |
| 21 | 100 |

TABLE 4-continued

| Compound | Rate of knocked-down insects (%) |
|---|---|
| 27 | 100 |
| 29 | 100 |
| 32 | 100 |
| 37 | 100 |
| 44 | 100 |
| 54 | 100 |

Biological test 3

Ten cockroaches (*Blattella germanica*) including five males and five females were left in a polyethylene cup (diameter: 9 cm) of which wall surface was thinly applied with vaseline. The cup was sealed with a 16-mesh nylon net and placed in a glass cylinder (inner diameter: 10 cm; depth: 37 cm). 0.1% (w/w) oil solution prepared from the present compounds according to Formulation example 7 was sprayed from an upper end of the cylinder with a spray gun at 0.6 atmospheric pressure. After twenty minutes, the insects were taken out and placed in another polyethylene cup with filter paper laid inside thereof. The insects were given water. After three days, the mortality of the insects was examined, and the results are shown in Table 5.

TABLE 5

| Compound | Mortality (%) |
|---|---|
| 1 | 100 |
| 2 | 100 |
| 5 | 100 |
| 6 | 100 |
| 9 | 100 |
| 12 | 100 |
| 14 | 100 |
| 17 | 100 |
| 20 | 100 |
| 21 | 100 |
| 22 | 100 |
| 24 | 100 |
| 29 | 100 |
| 37 | 100 |
| Oil solution containing no active ingredient | 0 |

Biological test 4

Mosquito-coil containing the present compound in an amount of 0.3% (w/w) was prepared according to Formulation example 10 for the present compounds. Ten female mosquitoes (*Culex pipiens pallens*) were left in a glass chamber (70cm×70 cm×70 cm: 0.34 m³) and 1.0 g of the mosquito-coil having both ends lit was placed in the glass chamber. After 24 minutes, the rate of knocked-down insects was examined, and the results are shown in Table 6.

TABLE 6

| Compound | Rate of knocked-down insects (%) |
|---|---|
| 1 | 100 |
| 2 | 100 |
| 5 | 100 |
| 6 | 100 |
| 8 | 100 |
| 9 | 100 |
| 10 | 100 |
| 11 | 100 |
| 12 | 100 |

TABLE 6-continued

| Compound | Rate of knocked-down insects (%) |
|---|---|
| 15 | 100 |
| 17 | 100 |
| 19 | 100 |
| 20 | 100 |
| 21 | 100 |
| 22 | 100 |
| 24 | 100 |
| 27 | 100 |
| 29 | 100 |
| 32 | 100 |
| 37 | 100 |
| 43 | 100 |
| 44 | 100 |
| 54 | 100 |
| 72 | 100 |

Biological test 5

After 0.64 ml of a 0.05% (w/v) acetone solution of the present compounds was dropped into an aluminum plate (bottom diameter: 7 cm), acetone was air-dried. Twenty female house flies (*Musca domestica*) were left in a polyethylene cup (diameter: 9 cm; depth: 4.5 cm), and the cup was sealed with a 16-mesh nylon net to prevent direct contact of the flies with the compound. The cup was placed upside down on the aluminum plate at 25° C. for 120 minutes. The cup was then removed from the aluminum plate, and water and feed were given to the flies. After twenty-four hours, the mortality was examined (two replicate), and the results are shown in Table 7.

TABLE 7

| Compound | Mortality (%) |
|---|---|
| 1 | 100 |
| 2 | 100 |
| 6 | 100 |
| 8 | 100 |
| 9 | 100 |
| 10 | 100 |
| 11 | 100 |
| 12 | 100 |
| 15 | 100 |
| 17 | 100 |
| 19 | 100 |
| 21 | 100 |
| 22 | 100 |
| 27 | 100 |
| 34 | 100 |
| 43 | 100 |
| 54 | 100 |
| A | 0 |
| B | 0 |
| C | 0 |

Biological test 6

Volatile agent prepared according to Formulation example 14 was suspended inner space of a polyethylene cup 1 (bottom diameter: 10 cm, diameter of opening: 12.5 cm; depth 9.5 cm; volume 950 cm³) placed upside down. Ten 21–28 day-instar larvae of *Tineola bisselliella* were left in another polyethylene cup 2 having the same size as the cup 1 and containing wool muslin cloth (2 cm×2 cm: approximately 100 mg) therein laid on the bottom thereof. The cups 1 and 2 were joined together and sealed at their openings, and left at 25° C. for one week. The cups were then opened, and the mortality of moths was examined. Table 8 shows the results.

TABLE 8

| Compound | Mortality (%) |
|---|---|
| 1 | 100 |
| 2 | 100 |
| 6 | 100 |
| 8 | 100 |
| 9 | 100 |
| 10 | 100 |
| 11 | 100 |
| 12 | 100 |
| 14 | 100 |
| 15 | 100 |
| 17 | 100 |
| 19 | 100 |
| 20 | 100 |
| 21 | 100 |
| 22 | 100 |
| 24 | 100 |
| 27 | 100 |
| 29 | 100 |
| 32 | 100 |
| 34 | 100 |
| 37 | 100 |
| 43 | 100 |
| 45 | 100 |
| 54 | 100 |
| A | 0 |
| B | 0 |
| C | 0 |

Biological test 7

Mite-repellent sheet prepared according to Formulation example 15 was cut into a circle of 4 cm in diameter. Approximately fifty mites (*Dermatophagoides farinae*) were left on the surface of the sheet. After one day, the number of mites, which were dead or trapped by an adhesive substance applied on the circumference of the sheet for preventing escape, was counted. The efficacy was evaluated by the ratio of the number of the dead or trapped mites to the total number of mites used. The results are shown in Table 9.

TABLE 9

| Compound | Efficacy (%) |
|---|---|
| 1 | 100 |
| 2 | 100 |
| 4 | 100 |
| 5 | 100 |
| 6 | 100 |
| 11 | 100 |
| 12 | 100 |
| 15 | 100 |
| 17 | 100 |
| 21 | 100 |
| 22 | 100 |
| 29 | 100 |
| 32 | 100 |
| 34 | 100 |
| 43 | 100 |
| 54 | 100 |
| no treatment | 8 |

What is claimed is:

1. A compound represented by the formula:

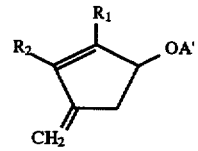

wherein $R_1$ represents a hydrogen atom or a methyl group; $R_2$ represents a 1-methyl-2-propenyl group, a 1-methyl-2-propynyl group, a 3,3-dihalogeno-1-methyl-2-propenyl group or a $C_1$–$C_6$ alkyl group which may be substituted with at least one halogen atom; and A' represents a hydrogen atom or a protecting group for a hydroxyl group.

2. A compound according to claim 1, wherein A' represents H, and said compound is an alcohol.

3. A compound according to claim 2, wherein $R_2$ represents an $C_1$–$C_6$ alkyl group which may be substituted with at least one halogen atom.

4. A compound according to claim 3, wherein $R_2$ is an ethyl group, a 2-fluoroethyl group, a 3-fluoropropyl group or a 2,2,2-trifluoroethyl group.

5. A compound according to claim 1, wherein said compound is an alcohol derivative in which A' represents a protecting group for a hydroxyl group.

6. A compound according to claim 5, wherein A' represents a ($C_1$–$C_2$)alkyl group substituted with ($C_1$–$C_2$)alkoxy group at the α-position, a tri($C_1$–$C_6$)alkylsilyl group, 2-tetrahydrofuranyl group or 2-tetrahydropyranyl group.

* * * * *